(12) United States Patent
Harris et al.

(10) Patent No.: US 9,848,871 B2
(45) Date of Patent: Dec. 26, 2017

(54) WOVEN AND FIBROUS MATERIALS FOR REINFORCING A STAPLE LINE

(71) Applicant: Ethicon LLC, Guaynabo, PR (US)

(72) Inventors: Jason L. Harris, Lebanon, OH (US); Bret W. Smith, Kings Mills, OH (US); Frederick E. Shelton, IV, Hillsboro, OH (US); Dennis D. Jamiolkowski, Long Valley, NJ (US)

(73) Assignee: Ethicon LLC, Guaynabo, PR (US)

( * ) Notice: Subject to any disclaimer, the term of this patent is extended or adjusted under 35 U.S.C. 154(b) by 706 days.

(21) Appl. No.: 14/300,804

(22) Filed: Jun. 10, 2014

(65) Prior Publication Data

US 2015/0351754 A1    Dec. 10, 2015

(51) Int. Cl.
*A61B 17/064* (2006.01)
*A61B 17/068* (2006.01)
*A61B 17/072* (2006.01)

(52) U.S. Cl.
CPC ........ *A61B 17/068* (2013.01); *A61B 17/0644* (2013.01); *A61B 17/0686* (2013.01); *A61B 17/07207* (2013.01); *A61B 17/07292* (2013.01)

(58) Field of Classification Search
CPC .............. A61B 17/068; A61B 17/0644; A61B 17/07292
See application file for complete search history.

(56) References Cited

U.S. PATENT DOCUMENTS

| | | | |
|---|---|---|---|
| 5,698,213 A | 12/1997 | Jamiolkowski et al. | |
| 5,700,583 A | 12/1997 | Jamiolkowski et al. | |
| 5,814,057 A * | 9/1998 | Oi | A61B 17/072 227/178.1 |
| 7,143,924 B2 | 12/2006 | Scirica et al. | |
| 7,143,925 B2 | 12/2006 | Shelton, IV et al. | |
| 7,772,352 B2 | 8/2010 | Bezwada | |
| 8,317,070 B2 | 11/2012 | Hueil et al. | |
| 8,393,514 B2 | 3/2013 | Shelton, IV et al. | |
| 8,551,058 B2 | 10/2013 | Measamer et al. | |
| 2006/0257458 A1 | 11/2006 | Gorman et al. | |
| 2007/0027550 A1 | 2/2007 | Farnsworth et al. | |
| 2009/0001122 A1 * | 1/2009 | Prommersberger | A61B 17/07207 227/176.1 |

(Continued)

FOREIGN PATENT DOCUMENTS

| | | |
|---|---|---|
| EP | 2591813 A2 | 5/2013 |
| WO | 2014016819 A1 | 1/2014 |

OTHER PUBLICATIONS

Chen et al. "Elastomeric Biomaterials for Tissue Engineering." Prog. Polymer. Sci. 38(2013):584-671.

(Continued)

*Primary Examiner* — Katherine Rodjom
(74) *Attorney, Agent, or Firm* — Mintz Levin Cohn Ferris Glovsky and Popeo, P.C.

(57) ABSTRACT

Adjunct materials and methods of using adjunct material to reinforce a staple line are provided. In general, an adjunct material can be used to maintain a seal in tissue and can prevent stapled tissue from tearing. In some embodiments, a surgical stapler can include a jaw having an adjunct material associated with the jaw. The adjunct material can be attached to tissue via staples deployed by the stapler. In some embodiments, an adjunct material can be a woven material having a single layer or multiple layers, and each layer can have different mechanical properties. In other embodiments, an adjunct material can have a single layer or multiple layers of nonwoven material, such as suture compressed into a three dimensional structure.

19 Claims, 25 Drawing Sheets

(56) References Cited

U.S. PATENT DOCUMENTS

| | | |
|---|---|---|
| 2009/0234193 A1 | 9/2009 | Weisenburgh, II et al. |
| 2009/0270686 A1 | 10/2009 | Duke et al. |
| 2011/0192882 A1 | 8/2011 | Hess et al. |
| 2012/0024934 A1 | 2/2012 | Shelton, IV et al. |
| 2012/0080335 A1 | 4/2012 | Shelton, IV et al. |
| 2012/0083835 A1 | 4/2012 | Shelton, IV et al. |
| 2012/0241498 A1 | 9/2012 | Gonzalez et al. |
| 2013/0112733 A1 | 5/2013 | Aranyi et al. |
| 2013/0146642 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0256365 A1 | 10/2013 | Shelton, IV et al. |
| 2013/0256372 A1 | 10/2013 | Baxter, III et al. |
| 2013/0256375 A1 | 10/2013 | Shelton, IV et al. |
| 2013/0256376 A1 | 10/2013 | Barton et al. |
| 2013/0256377 A1 | 10/2013 | Schmid et al. |
| 2014/0158741 A1 | 6/2014 | Woodard, Jr. et al. |
| 2015/0173756 A1 | 6/2015 | Baxter, III et al. |
| 2015/0272575 A1 | 10/2015 | Leimbach et al. |

OTHER PUBLICATIONS

Lim et al. "Fabrication and Evaluation of Poly(epsilon-caprolactone)/Silk Fibroin Blend Nanofibrous Scaffold." Biopolymers. 97(2012):265-275.

U.S. Appl. No. 13/763,192, filed Feb. 8, 2013.
U.S. Appl. No. 14/074,810, filed Nov. 8, 2013.
U.S. Appl. No. 14/074,884, filed Nov. 8, 2013.
U.S. Appl. No. 14/074,902, filed Nov. 8, 2013.
U.S. Appl. No. 14/075,438, filed Nov. 8, 2013.
U.S. Appl. No. 14/075,459, filed Nov. 8, 2013.
U.S. Appl. No. 14/300,793, filed Jun. 10, 2014.
U.S. Appl. No. 14/300,799, filed Jun. 10, 2014.
U.S. Appl. No. 14/300,801, filed Jun. 10, 2014.
U.S. Appl. No. 14/300,807, filed Jun. 10, 2014.
U.S. Appl. No. 14/300,811, filed Jun. 10, 2014.
U.S. Appl. No. 14/300,815, filed Jun. 10, 2014.
U.S. Appl. No. 14/300,817, filed Jun. 10, 2014.
U.S. Appl. No. 14/300,819, filed Jun. 10, 2014.
U.S. Appl. No. 14/300,820, filed Jun. 10, 2014.
U.S. Appl. No. 14/300,954, filed Jun. 10, 2014.
Zhao et al. "Biodegradable Fibrous Scaffolds Composed of Gelatin Coated Poly(?-caprolactone) Prepared by Coaxial Elecrospinning." J. Biomed. Mater. Res. 83A(2007):372-382.
European Search Report for Application No. 15171457.3 dated Oct. 8, 2015.
International Search Report and Written Opinion for Application No. PCT/US2015/030933 dated Jul. 24, 2015.

* cited by examiner

FIG. 1 <u>PRIOR ART</u>

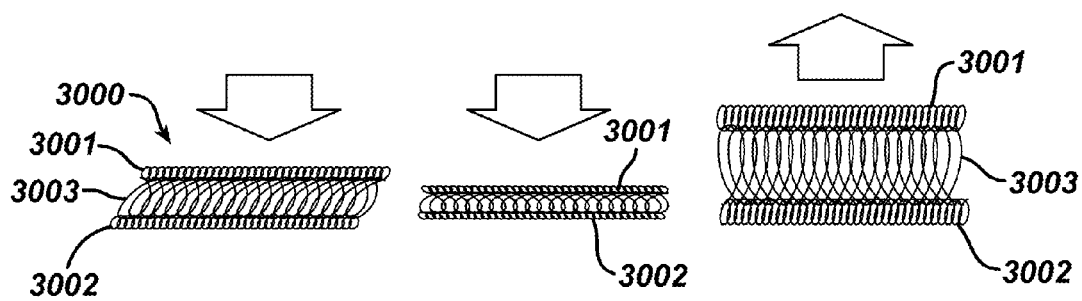
*FIG. 17A*  *FIG. 17B*  *FIG. 17C*

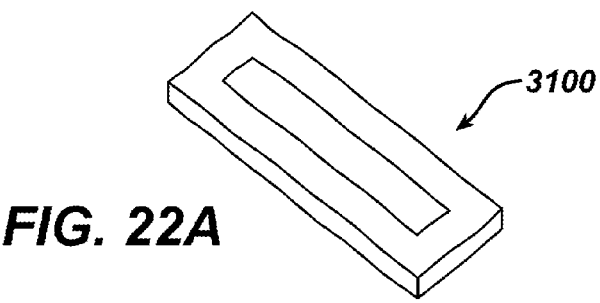
FIG. 22A
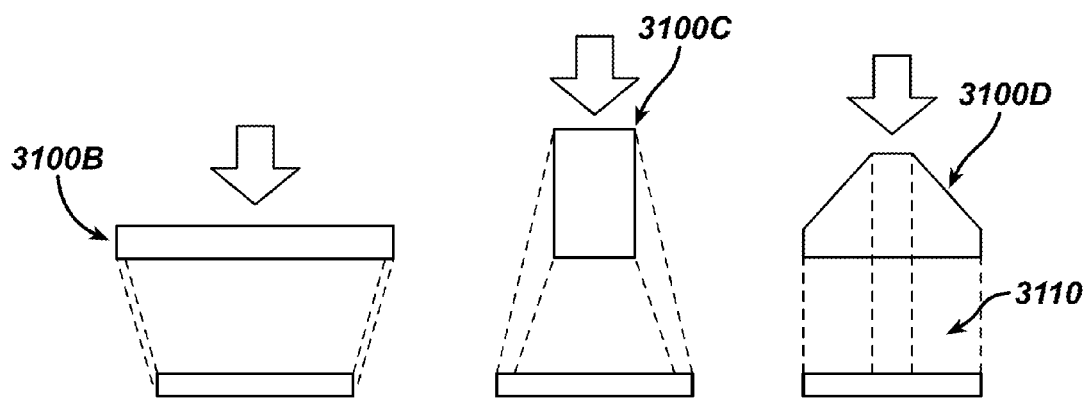
FIG. 22B  FIG. 22C  FIG. 22D

WOVEN AND FIBROUS MATERIALS FOR REINFORCING A STAPLE LINE

FIELD

The subject matter disclosed herein relates to methods and devices for reinforcing a staple line.

BACKGROUND

Surgical staplers are used in surgical procedures to seal, divide, and/or transect tissues in the body by closing openings in tissue, blood vessels, ducts, shunts, or other objects or body parts involved in the particular procedure. The openings can be naturally occurring, such as passageways in blood vessels, airways or an internal lumen or organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate flexible or rigid shaft having a pair of opposed jaws formed on an end thereof for holding and forming staples therebetween. At least one of the opposed jaws is movable relative to the other jaw. In the case of laparoscopic surgery, often one jaw is fixed and the other is movable. In some devices (for example an open linear stapler), the opposed jaws can be separated by the operator and reassembled providing the relative motion needed for tissue placement. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut the stapled tissue between the stapled rows. Placement of the device, manipulation of components or systems of the device, and other actuations of the device such as articulation, firing, etc. can be accomplished in a variety of ways, such as electromechanically, mechanically, or hydraulically.

While surgical staplers have improved over the years, a number of problems can potentially arise. Although rare, as illustrated in FIG. 1, one problem is that leaks can occur due to staples S forming tears H when penetrating a tissue T or other object in which the staples S are disposed. Blood, air, gastrointestinal fluids, and other fluids can seep through the tears H formed by the staples S, even after the staples S are fully formed. The tissue T being treated can also become inflamed due to the manipulations and deformations that can occur during stapling. Still further, staples, as well as other objects and materials implanted during stapling procedures, generally lack the same characteristics as tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

Accordingly, there remains a need for methods and devices for reinforcing a staple line.

SUMMARY

Adjunct materials for use with end effectors like surgical stapling devices, and methods for using the same, are generally provided. In some embodiments a staple cartridge assembly for use with a surgical stapler can include a cartridge body having a plurality of staple cavities configured to seat staples therein and a biocompatible, compressible adjunct material releasably retained on the cartridge body. The adjunct material can be configured to be delivered to tissue by deployment of the staples in the cartridge body. The adjunct material can be a woven matrix such that the material can have a compressible elastic core layer configured to compress upon application of a compressive force and expand upon removal of the compressive force, and at least one flexible supportive layer coupled to at least one side of the compressible elastic core layer. In some embodiments, the adjunct material can contain a therapeutic substance such as a drug or other medicament. Additionally, in some embodiments the adjunct material can be selectively strengthened in certain areas.

The adjunct material can be a woven matrix such that the adjunct material will provide tissue support for tissue within and surrounding the staple line. In one embodiment, woven 3-D structures are created and compressed or otherwise formed into different shapes that have a higher density and different mechanical properties. This woven structure allows the adjunct to have different material characteristics in the compressed and uncompressed states. The amount of material and degree of compression can be used to determine the mechanical properties of the resultant brick. Multiple fiber types can be used in the weave to give it additional properties of interest including compressibility, abrasion resistance, bioabsorption profile, fluid absorption profile, substance elution characteristics, ability to be cut with a knife, ability to swell.

In other aspects, an end effector for a surgical instrument is provided. The end effector can include a first jaw having a cartridge body removably attached hereto, the cartridge body having a plurality of staple cavities configured to seat staples therein, a second jaw having an anvil with a plurality of staples forming openings formed therein. The adjunct material can be releasably retained on at least one of the tissue contacting surfaces of the cartridge body and the anvil so that it can be delivered to tissue upon deployment of the staples. The adjunct material can be comprised of a compressible elastic region configured to compress upon application of a compressive force and expand upon removal of the compressive force, and at least one flexible supportive region adjacent to the compressible elastic region.

In other aspects a method for stapling tissue is provided. The method can include engaging tissue between a cartridge assembly and an anvil of an end effector, one of which has an adjunct material releasable retained thereon, and actuating the end effector to eject staples from the cartridge assembly into tissue. The staples can extend through the adjunct material to maintain the adjunct material at the surgical site.

BRIEF DESCRIPTION OF THE DRAWINGS

The invention will be more fully understood from the following detailed description taken in conjunction with the accompanying drawings, in which:

FIG. 17A is a side view of a woven adjunct material before a compressive force is applied thereto;

FIG. 17B is a side view of a woven adjunct material of FIG. 17A having a compressive force applied thereto;

FIG. 17C is a side view of the woven adjunct material of FIG. 17A after the compressive force is released therefrom;

FIG. 22A is a perspective view of a fleece adjunct material;

FIG. 22B is a perspective view of a longitudinal fleece adjunct material with a compressive force applied thereto.

FIG. 22C is a perspective view of a rectangular fleece adjunct material with a compressive force applied thereto.

FIG. 22D is a perspective view of a polygonal fleece adjunct material with a compressive force applied thereto.

DETAILED DESCRIPTION

Figure 1:
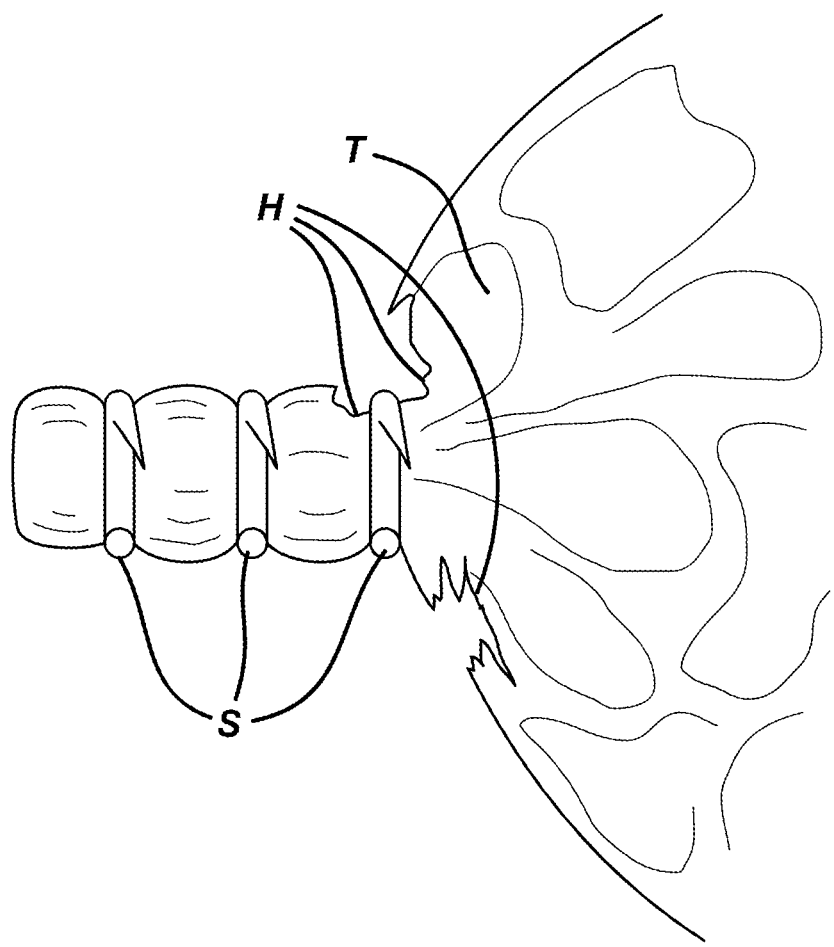
FIG. 1 is a side view of damaged stapled tissue.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of such devices and methods is defined solely by the claims. The features illustrated or described in connection with one exemplary embodiment may be combined with the features of other embodiments. Such modifications and variations are intended to be included within the scope of the devices and methods described herein. Further, in the present disclosure, like-numbered components of the various embodiments generally have similar features when those components are of a similar nature and/or serve a similar purpose.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the methods, apparatus, devices, and systems described herein.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

It can be desirable to use one or more biologic materials and/or synthetic materials, collectively referred to herein as "adjunct materials," in conjunction with surgical instruments to help improve surgical procedures. These biologic materials may be derived from human and/or animal sources. A person skilled in the art may refer to these types of materials as buttress materials as well as adjunct materials.

Various exemplary devices and methods are provided for performing surgical procedures. In some embodiments, the devices and methods are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

End effectors of the surgical instruments as described herein can be configured to deliver one or more synthetic materials and/or biologic materials, collectively referred to herein as "adjunct materials," to a surgical site to help improve surgical procedures. These biologic materials may be derived from human and/or animal sources. While a variety of different end effectors can benefit from the use of adjunct materials, in some exemplary embodiments the end effector can be a surgical stapler. When used in conjunction with a surgical stapler, the adjunct material(s) can be disposed between and/or on jaws of the stapler, incorporated into a staple cartridge disposed in the jaws, or otherwise placed in proximity to the staples. When staples are deployed, the adjunct material(s) can remain at the treatment site with the staples, in turn providing a number of benefits. In some instances, the adjunct material(s) can be used to help seal holes formed by staples as they are implanted into tissue, blood vessels, and various other objects or body parts, and/or can be used to provide tissue reinforcement at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct material(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct material(s) can be configured to wick or absorb beneficial fluids, e.g., sealants, blood, glues, that further promote healing, and in some instances, the adjunct material(s) can be configured to degrade to form a gel, e.g., a sealant, that further promotes healing. In some instances, the adjunct may carry materials that when placed into a wet environment (e.g., blood, water, saline, or other bodily fluids) form a sealant to create a seal (e.g., human or animal derived fibrinogen and thrombin can be lyophilized into a powder form that when mixed with water creates a sealant). Still further, the material(s) can help reduce inflammation, promote cell growth, and otherwise improve healing.

Figure 2:
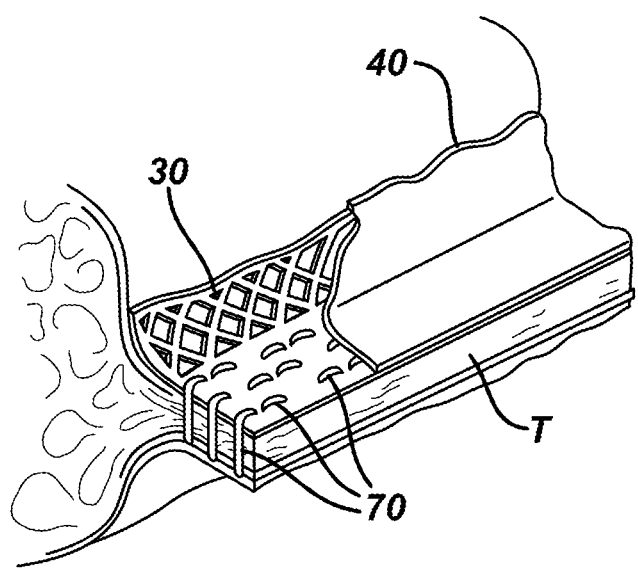
FIG. 2 is a perspective view of one embodiment of an adjunct material as described herein that is fixed to stapled tissue.

FIG. 2 illustrates one embodiment of an adjunct material that includes a porous buttress 30 that can be fixed to a tissue T to be treated by a surgical stapler and that remains at the treatment site with staples 70. The buttress 30 can be made from one or more absorbent materials and can be stamped, pressed, cut, molded, woven, melted, blown, comprised from composite structures and/or methods or otherwise shaped to facilitate absorption, reinforcement, delivery and/or retention of beneficial fluids such as sealants, glues, blood, etc. The absorption and/or retention of beneficial fluids, for example a fibrin sealant 40, at the treatment site can further help to prevent leaks and to reinforce the buttress 30.

In use, the adjunct material can come pre-loaded onto the device and/or the staple cartridge, while in other instances the adjunct material can be packaged separately. In instances in which the adjunct material comes pre-loaded onto the device and/or the staple cartridge, the stapling procedure can be carried out as known to those skilled in the art. For example, in some instances the firing of the device can be enough to disassociate the adjunct material from the device and/or the staple cartridge, thereby requiring no further action by the clinician. In other instances any remaining connection or retention member associating the adjunct material with the device and/or the staple cartridge can be removed prior to removing the instrument from the surgical site, thereby leaving the adjunct material at the surgical site. In instances in which the adjunct material is packaged separately, the material can be releasably coupled to at least one of a component of the end effector and the staple cartridge prior to firing the device. The adjunct material may be refrigerated, and thus removed from the refrigerator and the related packaging, and then coupled to the device using a connection or retention member as described herein or otherwise known to those skilled in the art. The stapling procedure can then be carried out as known to those skilled in the art, and if necessary, the adjunct material can be disassociated with the device as described above.

A person skilled in the art will recognize a variety of other ways by which the adjunct material can be temporarily retained with respect to the end effector. In various embodiments a connection or retention member can be configured to be released from an end effector and deployed along with a piece of adjunct material. In at least one embodiment, head portions of retention members can be configured to be separated from body portions of retention members such that the head portions can be deployed with the adjunct material while the body portions remain attached to the end effector. In other various embodiments, the entirety of the retention members can remain engaged with the end effector when the adjunct material is detached from the end effector.

Adjunct materials described herein may be used in any surgery where a surgical stapler or other instrument creating tissue punctures is utilized. In some embodiments, adjunct materials described herein may be used for sealing staple punctures created when a surgical stapler is used in lung surgery. When surgery is performed on a lung (e.g., lobectomy, segmentectomy, wedge resection, lung volume reduction surgery, etc.), the lung is typically collapsed, and the required procedure, including application of the stapler to tissue to be removed, is then performed on the collapsed lung. After the procedure is completed, the collapsed lung is re-inflated. The re-inflation of the lung stretches the lung parenchyma, which may result in increased stress at a junction between the stapled tissue and surrounding tissue that was not punctured. Furthermore, airtight sealing is required for the staple punctures of the lung. Such airtight sealing may be difficult to achieve due to lung tissue movement. While leaks around staple punctures typically heal within approximately five days, in some cases, staple punctures may persist for longer periods of time, such as, for example, up to six months.

Accordingly, some embodiments provide adjunct material that may be used to seal staple punctures created by a surgical stapler used to secure lung tissue. However, it should be appreciated that the adjunct materials can also be used to seal punctures created by surgical staplers used to secure any other type of tissue, such as, for example, blood vessels, intestinal, stomach and esophageal tissue.

Surgical Stapling Instrument

Figure 3:
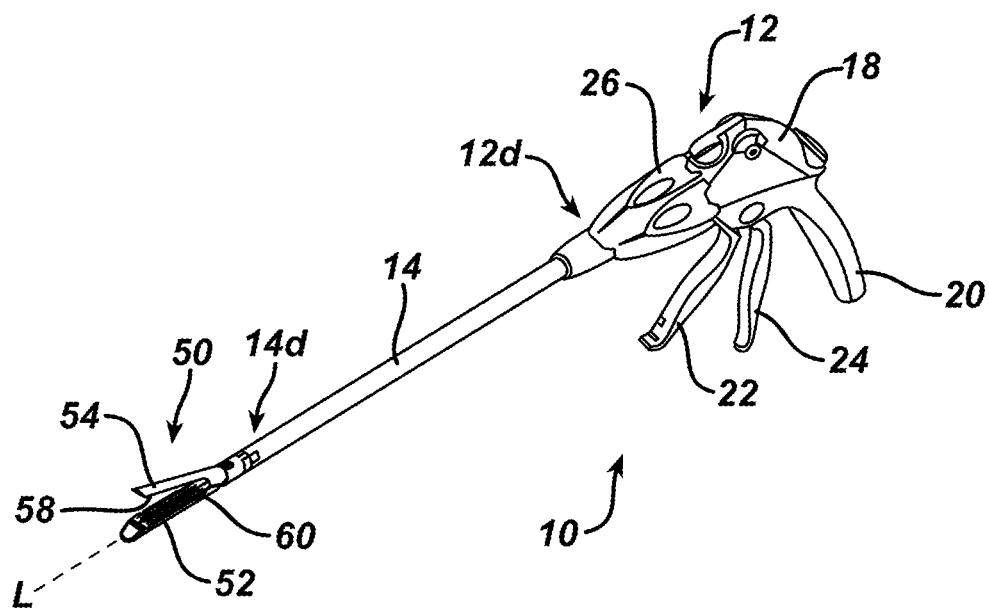
FIG. 3 is a perspective view of a prior art surgical instrument which can be used with one or more adjunct materials.

While a variety of surgical instruments can be used in conjunction with the adjunct materials disclosed herein, FIG. 3 illustrates one, non-limiting exemplary embodiment of a surgical stapler 10 suitable for use with one or more adjunct materials. The instrument 10 generally includes a handle assembly 12, a shaft 14 extending distally from a distal end 12d of the handle assembly 12, and an end effector 50 at a distal end 14d of the shaft 14. Because the illustrated embodiment is a surgical stapler, the end effector 50 has jaws 52, 54, although other types of end effectors can be used with the shaft 14, handle assembly 12, and components associated with the same. The surgical stapler 10 includes opposed lower and upper jaws 52, 54 with the lower jaw 52 including a staple channel 56 (FIG. 4) configured to support a staple cartridge 60, and the upper jaw 54 having an inner surface 58 that faces the lower jaw 52 and that is configured to operate as an anvil to help deploy staples 70 of the staple cartridge 60. The jaws 52, 54 are configured to move relative to one another to clamp tissue or other objects disposed therebetween, and components of a firing system can be configured to pass through at least a portion of the end effector 50 to eject the staples into the clamped tissue. In various embodiments a knife blade 81 can be associated with the firing system to cut tissue during the stapling procedure. At least one of the opposed lower and upper jaws 52, 54 will be moveable relative to the other lower and upper jaws 52, 54. At least one of the opposed lower and upper jaws 52, 54 may be fixed or otherwise immovable. In some embodiments, both of the opposed lower and upper jaws 52, 54 will be movable.

Operation of the end effector 50 can begin with input from a clinician at the handle assembly 12. The handle assembly 12 can have many different configurations designed to manipulate and operate the end effector 50 associated therewith. In the illustrated embodiment, the handle assembly 12 has a pistol-grip type housing 18 with a variety of mechanical and/or electrical components disposed therein to operate various features of the instrument. For example, the handle assembly 12 can include a rotation knob 26 mounted adjacent a distal end 12d thereof which can facilitate rotation of the shaft 14 and/or the end effector 50 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 52, 54 to collapse towards each other and to thereby clamp tissue therebetween. Movement of the firing trigger 24 can actuate the firing system, described below, which can cause the ejection of staples from a staple cartridge disposed therein and/or the advancement the knife blade 81 to sever tissue captured between the jaws 52, 54. A person skilled in the art will recognize that various configurations of components for a firing system, mechanical, hydraulic, pneumatic, electro-mechanical, robotic, or otherwise, can be used to eject staples and/or cut tissue, and thus a detailed explanation of the same is unnecessary.

Figure 4:
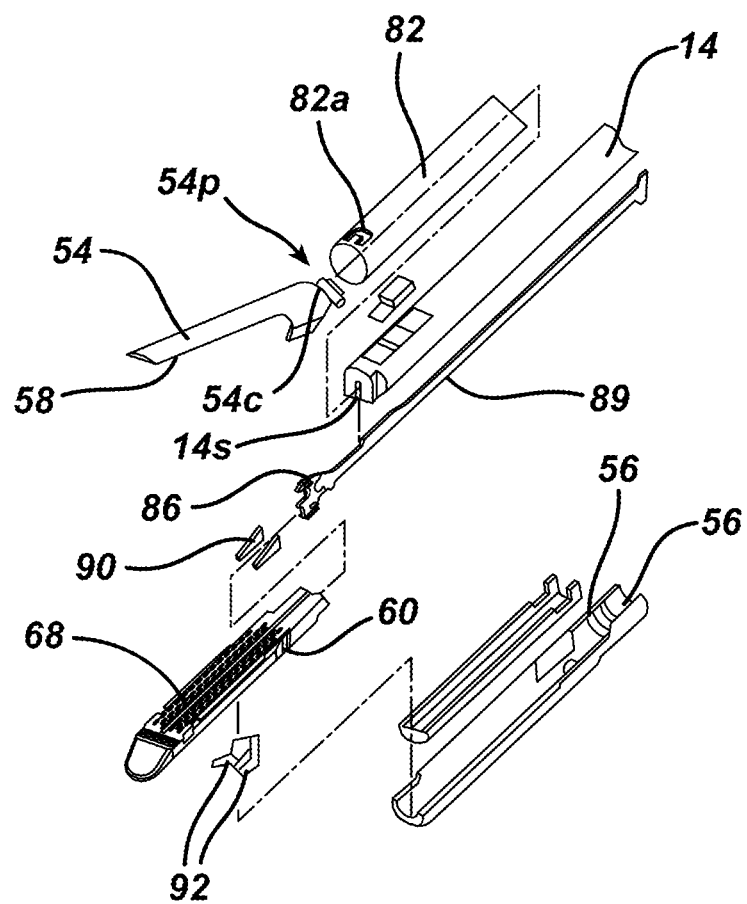
FIG. 4 is an exploded perspective view of an end effector and a distal end of a shaft of the instrument of FIG. 3.

As shown in more detail in FIG. 4, the end effector 50 of the illustrated embodiment is a surgical stapling tool having a lower jaw 52 that serves as a cartridge assembly or carrier and an opposed upper jaw 54 that serves as an anvil. The staple cartridge 60, having a plurality of staples 70 therein, is supported in a staple tray 57, which in turn is supported within the cartridge channel of the lower jaw 52. The upper jaw 54 has a plurality of staple forming pockets 66 (FIG. 11), each of which is positioned above a corresponding staple from the plurality of staples 70 contained within the staple cartridge 60. The upper jaw 54 can be connected to the lower jaw 52 in a variety of ways, although in the illustrated embodiment the upper jaw 54 has a proximal pivoting end 54p that is pivotally received within a proximal end 56p of the staple channel 56, just distal to its engagement to the shaft 14. When the upper jaw 54 is pivoted downwardly, the upper jaw 54 moves the anvil surface 58 and the staple forming pockets 66 formed thereon move toward the opposing staple cartridge 60.

Various clamping components can be used to effect opening and closing of the jaws 52, 54 to selectively clamp tissue therebetween. In the illustrated embodiment, the pivoting end 54p of the upper jaw 54 includes a closure feature 54c distal to its pivotal attachment with the staple channel 56. Thus, a closure tube 82, whose distal end includes a horseshoe aperture 82a that engages the closure feature 54c, selectively imparts an opening motion to the upper jaw 54 during proximal longitudinal motion and a closing motion to the upper jaw 54 during distal longitudinal motion of the closure tube 82 in response to the clamping trigger 22. It will be appreciated by a person skilled in the art that opening and closure of the end effector 50 may be effected by relative motion of the lower jaw 52 with respect to the upper jaw 54, relative motion of the upper jaw 54 with respect to the lower jaw 52, or by motion of both jaws 52, 54 with respect to one another.

Figure 5:
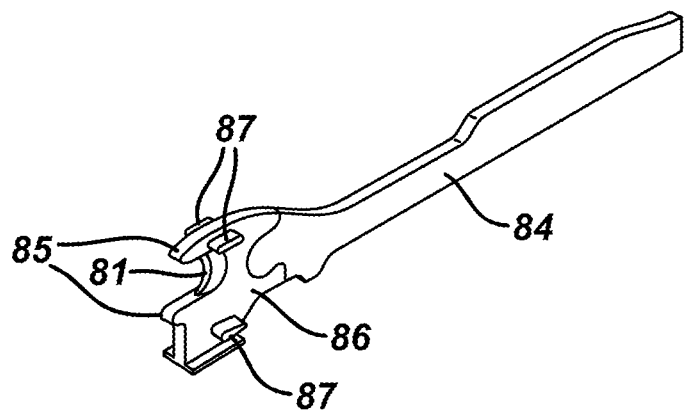
FIG. 5 is a perspective view of an E-beam component of the instrument of FIG. 3.

The firing components of the illustrated embodiment can include a firing bar 84, as shown in FIG. 5, having an E-beam 86 on a distal end thereof. The firing bar 84 is encompassed within the shaft 14, for example in a longitudinal firing bar slot 14s of the shaft 14, and guided by a firing motion from the handle 12. Actuation of the firing trigger 24 can affect distal motion of the E-beam 86 through at least a portion of the end effector 50 to thereby cause the firing of staples 70 contained within the staple cartridge 60. In the illustrated embodiment, guides 85 projecting from a distal end of the E-Beam 86 can engage a wedge sled 90, which in turn can push staple drivers 92 upwardly through staple cavities 68 formed in the staple cartridge 60. Upward movement of the staple drivers 92 applies an upward force on each of the plurality of staples 70 within the cartridge 60 to thereby push the staples 70 upwardly against the anvil surface 58 of the upper jaw 54 and to create formed staples 70'.

In addition to causing the firing of staples, the E-beam 86 can be configured to facilitate closure of the jaws 52, 54, spacing of the upper jaw 54 from the staple cartridge 60, and/or severing of tissue captured between the jaws 52, 54. In particular, a pair of top pins 87 and a pair of bottom pins 89 can engage one or both of the upper and lower jaws 52, 54 to compress the jaws 52, 54 toward one another as the firing bar 84 advances through the end effector 50. Simultaneously, a knife 81 extending between the top and bottom pins 87, 89 can be configured to sever tissue captured between the jaws 52, 54.

In use, the surgical stapler 10 can be disposed in a cannula or port and disposed at a surgical site. A tissue to be cut and stapled can be placed between the jaws 52, 54 of the surgical stapler 10. Features of the stapler 10 can be maneuvered as desired by the clinician to achieve a desired location of the jaws 52, 54 at the surgical site and the tissue with respect to the jaws 52, 54. After appropriate positioning has been achieved, the clamping trigger 22 can be pulled toward the stationary handle 20 to actuate the clamping system. The trigger 22 can cause components of the clamping system to operate such that the closure tube 82 advances distally through at least a portion of the shaft 14 to cause at least one of the jaws 52, 54 to collapse towards the other to clamp the tissue disposed therebetween. Thereafter, the trigger 24 can be pulled toward the stationary handle 20 to cause components of the firing system to operate such that the firing bar 84 and/or the E-beam 86 are advanced distally through at least a portion of the end effector 50 to effect the firing of staples 70 and optionally to sever the tissue captured between the jaws 52, 54.

Figure 6:
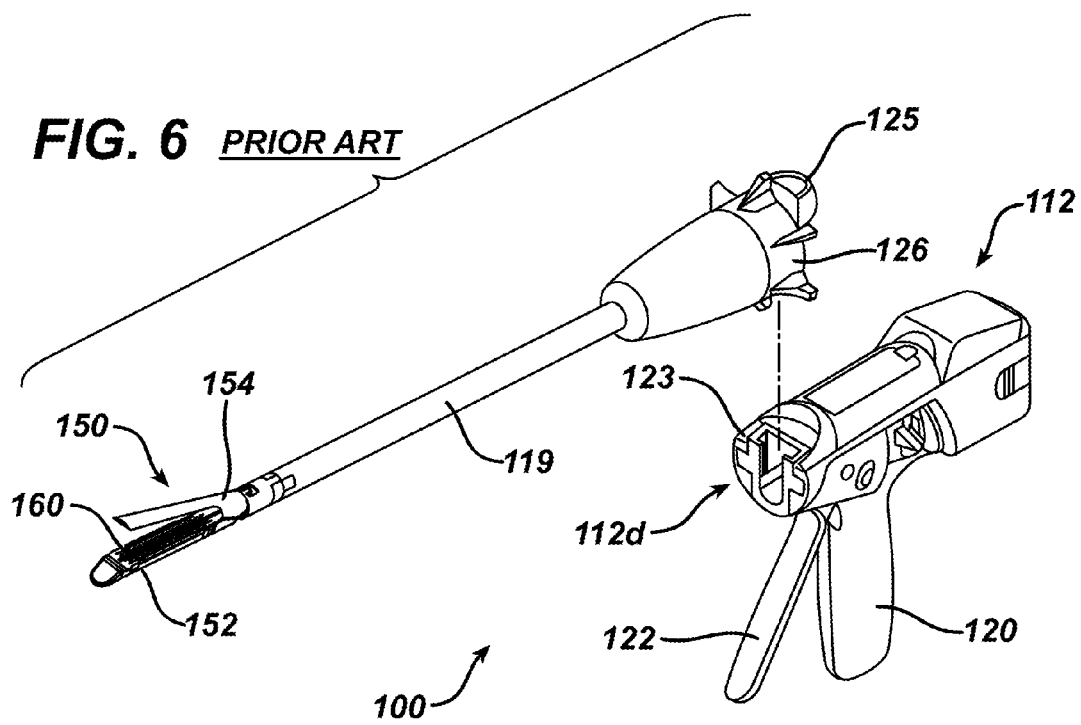
FIG. 6 is a perspective view of another prior art surgical instrument which can be used with one or more adjunct materials.

Another embodiment of a surgical instrument 100 is illustrated in FIG. 6. Like surgical instrument 10, surgical instrument 100 includes a handle assembly 112 with a shaft 114 extending distally therefrom and having an end effector 150 on a distal end thereof for treating tissue. Upper and lower jaws 154, 152 of the end effector 150 can be configured to capture tissue therebetween, staple the tissue by firing of staples from a cartridge 160 disposed in the lower jaw 154, and/or to create an incision in the tissue. In this embodiment, an attachment portion 116 on a proximal end of the shaft 114 can be configured to allow for removable attachment of the shaft 114 and the end effector 150 to the handle assembly 112. In particular, mating features 125 of the attachment portion 116 can mate to complementary mating features 123 of the handle assembly 112. The mating features 123, 125 can be configured to couple together via, e.g., a snap fit coupling, a bayonet type coupling, etc., although any number of complementary mating features and any type of coupling can be used to removably couple the shaft 114 to the handle assembly 112. Although the entire shaft 114 of the illustrated embodiment is configured to be detachable from the handle assembly 112, in some embodiments the attachment portion 116 can be configured to allow for detachment of only a distal portion of the shaft 114. Detachable coupling of the shaft 114 and/or the end effector 150 can allow for selective attachment of a desired end effector 150 for a particular procedure, and/or for reuse of the handle assembly 112 for multiple different procedures.

The handle assembly 112 can have one or more features thereon to manipulate and operate the end effector 150. By way of non-limiting example, a rotation knob 126 mounted on a distal end of the handle assembly 112 can facilitate rotation of the shaft 114 and/or the end effector 150 with respect to the handle assembly 112. The handle assembly 112 can further include clamping components as part of a clamping system actuated by trigger 122 and firing components as part of a firing system that can also be actuated by the trigger 122. Thus, in some embodiments, movement of the trigger 122 toward a stationary handle 120 through a first range of motion can actuate clamping components to cause opposed jaws 152, 154 to approximate toward one another to a closed position. Further movement of the trigger 122 toward the stationary handle 120 through a second range of motion can actuate firing components to cause the ejection of staples from the staple cartridge 160 and/or the advancement of a knife to sever tissue captured between the jaws 152, 154.

Figure 7:
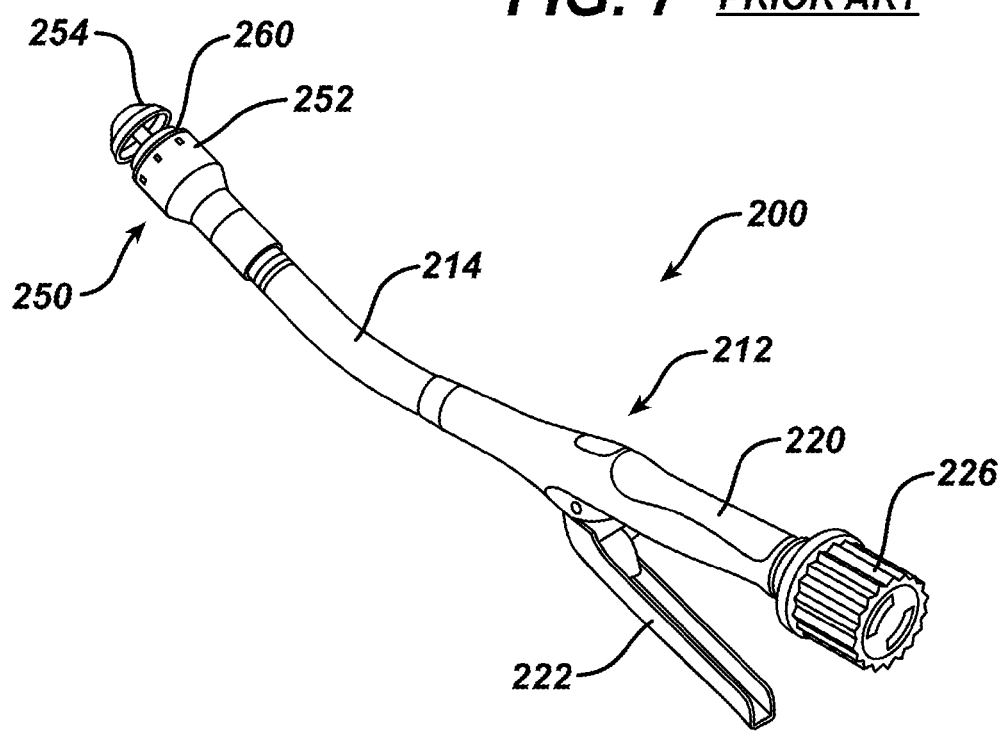
FIG. 7 is a perspective view of another prior art surgical instrument which can be used with one or more adjunct materials.

Yet another embodiment of a surgical instrument 200 is illustrated in FIG. 7. Like surgical instruments 10 and 100, surgical instrument 200 includes a handle assembly 212 with a shaft 214 extending distally therefrom and having an end effector 250 on a distal end thereof for treating tissue. The end effector 250 can include a cartridge assembly 252 and an anvil 254, each having a tissue-contacting surface 260$p$, 260$d$ that is substantially circular in shape. The cartridge assembly 252 and anvil 254 can be coupled together via a shaft 262 extending from the anvil 254 to the handle assembly 212 of the stapler 200, and manipulating an actuator 222 on the handle assembly 220 can retract and advance the shaft 262 to move the anvil 254 relative to the cartridge assembly 252. In one embodiment, the shaft 262 can be formed of first and second portions (not shown) configured to releasably couple together to allow the anvil 254 to be detached from the cartridge assembly 252, allowing greater flexibility in positioning the anvil 254 and the cartridge assembly 252 in a body. For example, the first portion of the shaft can be disposed within the cartridge assembly 252 and extend distally outside of the cartridge assembly 252, terminating in a distal mating feature. The second portion of the shaft 214 can be disposed within the anvil 254 and extend proximally outside of the cartridge assembly 252, terminating in a proximal mating feature. In use, the proximal and distal mating features can be coupled together to allow the anvil 254 and cartridge assembly 252 to move relative to one another. The anvil 254 and cartridge assembly 252 can perform various functions and can be configured to capture tissue therebetween, staple the tissue by firing of staples from a cartridge assembly 252 and/or can create an incision in the tissue. In general, the cartridge assembly 252 can house a cartridge containing the staples and can deploy staples against the anvil 254 to form a circular pattern of staples around a circumference of a tubular body organ.

The handle assembly 212 of the stapler 200 can have various actuators disposed thereon that can control movement of the stapler. For example, the handle assembly 212 can have a rotation knob 226 disposed thereon to facilitate positioning of the end effector 250 via rotation, and/or a trigger 222 for actuation of the end effector 250. Movement of the trigger 222 through a first range of motion can actuate components of a clamping system to approximate the jaws, i.e. move the anvil 254 toward the cartridge assembly 252. Movement of the trigger 222 through a second range of motion can actuate components of a firing system to cause the staples to deploy from the staple cartridge assembly 252 and/or cause advancement of a knife to sever tissue captured between the cartridge assembly 252 and the anvil 254.

The illustrated embodiments of surgical stapling instruments 10, 100, and 200 provide only a few examples of many different configurations, and associated methods of use, that can be used in conjunction with the disclosures provided herein. Although the illustrated embodiments are all configured for use in minimally invasive procedures, it will be appreciated that instruments configured for use in open surgical procedures, e.g., open linear staplers as described in U.S. Pat. No. 8,317,070, can be used in conjunction with the disclosures provided herein. Greater detail on the illustrated embodiments, as well as additional exemplary embodiments of surgical staplers, components thereof, and their related methods of use, that can be used in accordance with the present disclosure include those devices, components, and methods provided for in U.S. Publication No. 2013/0256377, U.S. Pat. Nos. 8,393,514, 8,317,070, 7,143,925, U.S. patent application Ser. No. 14/074,884, entitled "Sealing Materials for Use in Surgical Procedures," and filed on Nov. 8, 2013, U.S. patent application Ser. No. 14/074,810, entitled "Hybrid Adjunct Materials for Use in Surgical Stapling," and filed on Nov. 8, 2013, U.S. patent application Ser. No. 14/075,438, entitled "Positively Charged Implantable Materials and Method of Forming the Same," and filed on Nov. 8, 2013, U.S. patent application Ser. No. 14/075,459, entitled "Tissue Ingrowth Materials and Method of Using the Same," and filed on Nov. 8, 2013, U.S. patent application Ser. No. 14/074,902, entitled "Hybrid Adjunct Materials for Use in Surgical Stapling," and filed on Nov. 8, 2013, U.S. patent application Ser. No. 14/226,142, entitled "Surgical Instrument Comprising a Sensor System," and filed on Mar. 26, 2014, each of which is incorporated by reference herein in its entirety.

End Effector Variations

End effectors of the surgical stapling instruments described herein can have one or more features for adjusting an amount of compression applied to tissue captured by the end effector. In some embodiments, the end effector can be configured to create a desired compression profile in tissue captured therein, for example a profile that helps to minimize bleeding, tearing, and/or leakage of the treated tissue. By way of non-limiting example, the desired tissue compression profile can be obtained using variations in a gap between upper and lower jaws of the end effector and/or variations in the orientation, size, and/or shape of staples applied to tissue by the end effector. As described in detail herein, adjunct material(s) used in conjunction with such an end effector can be configured to assist in creating the desired tissue compression profile and/or to accommodate features used to create the desired tissue compression profile.

Any such variations described herein can be used alone or together to provide the desired tissue compression profile. Although exemplary end effectors and components thereof are described in conjunction with a particular surgical instrument, e.g., instruments 10, 100, and 200, it will be appreciated that the end effectors and components thereof can be configured for use with other embodiments of surgical instruments as described herein.

Figure 8:
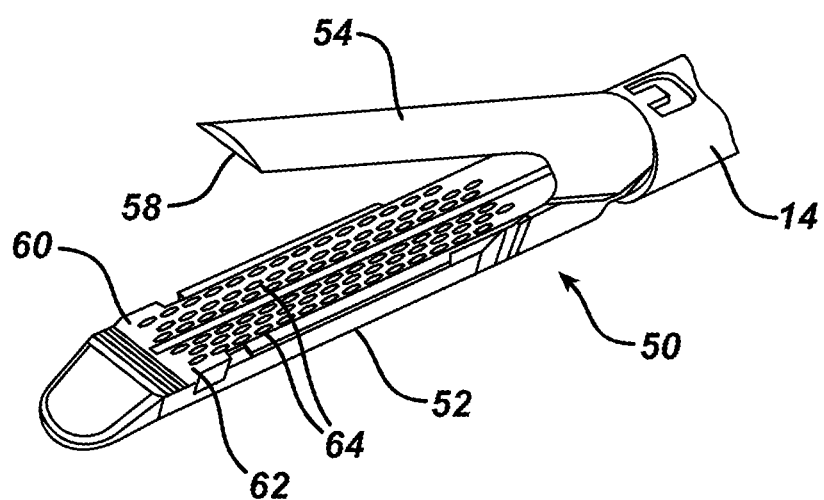
FIG. 8 is a perspective view of the end effector of FIG. 4.

In some embodiments, a staple cartridge disposed within an end effector of a surgical stapling instrument can have a first portion configured to compress tissue captured by the end effector more than a second portion when the end effector is in a closed position. The first portion of the cartridge can be spaced longitudinally and/or laterally from the second portion to create a desired compression gradient. For example, as shown in FIGS. 4 and 8, the staple cartridge 60 can have a stepped tissue contacting surface. In particular, the cartridge 60 can have an inner tissue contacting surface 62 and outer tissue contacting surfaces 64 that extend upwardly to a taller height than the inner tissue contacting surface 62. In this way, when the upper jaw 54 is in the closed position in close approximation with the cartridge 60, the anvil surface 58 can be configured to compress the outer surfaces 64 more than the inner surface 62 due to the taller height of the outer surfaces 64. In some circumstances, including circumstances where tissue positioned between the anvil surface 58 and the cartridge 60 has a constant, or at least substantially constant, thickness, the pressure generated within the tissue can be greater at outer portions of the end effector 50 than at inner portions of the end effector 50. Whereas a compression gradient generated by the cartridge 60 varies in a stepped manner, it will be appreciated by a person skilled in the art that a gradual compression gradient can be generated within the tissue by a gradual increase in height of various portions of the cartridge 60. It will also be appreciated that a compression gradient can be obtained by variations in height of the anvil surface 58, alone or in combination with height variations of the cartridge 60, and that height variations can be spaced laterally and/or longitudinally across the end effector 50.

Figure 9:
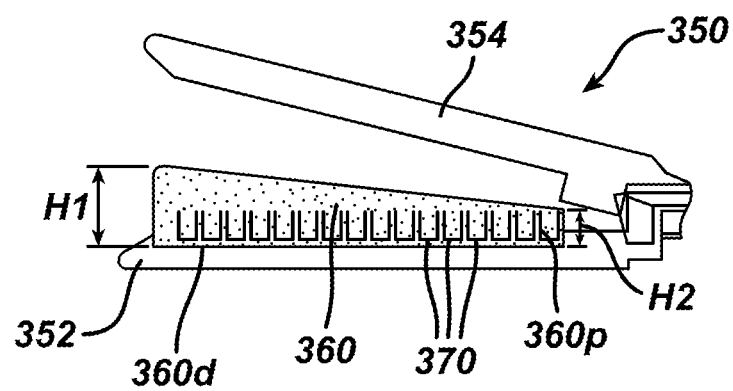
FIG. 9 is a side view of a prior art end effector having an implantable staple cartridge therein.

In some embodiments, one or more adjunct materials fixed to an end effector of a surgical stapling instrument can be used to create a desired compression profile in tissue captured by the end effector. Referring now to FIG. 9, a compressible, implantable staple cartridge 360 can be formed from one or more adjunct materials as described herein and can be configured to be seated within an end effector of a surgical instrument, e.g., an end effector 350. The cartridge 360 can have a height that decreases from a tallest height H1 at a distal end 360d thereof to a smallest height H2 at a proximal end 360p thereof. In this way, when an upper jaw 354 of the end effector 350 is in the closed position in close approximation with the cartridge 360, an upper jaw 354 of the end effector 350 can be configured to compress the distal end 360d more than the proximal end 360p. Although the compression gradient created in the captured tissue by the cartridge 360 decreases linearly from the distal end 360d to the proximal end 360p, it will appreciated by a person skilled in the art that any compression gradient can be created by different shapes of the cartridge 360. In at least one embodiment, a thickness of the cartridge 360 can vary across its width, similar to the cartridge 360.

Figure 10:
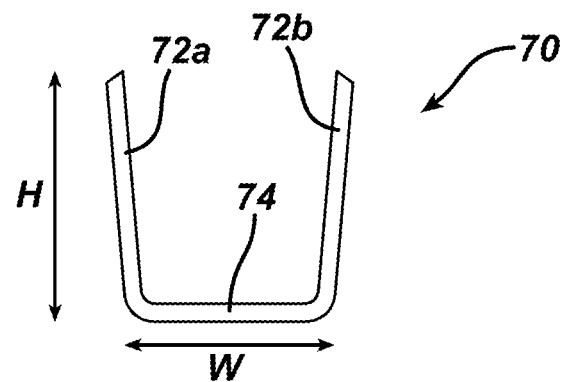
FIG. 10 is a side view of a prior art staple.
Figure 11:
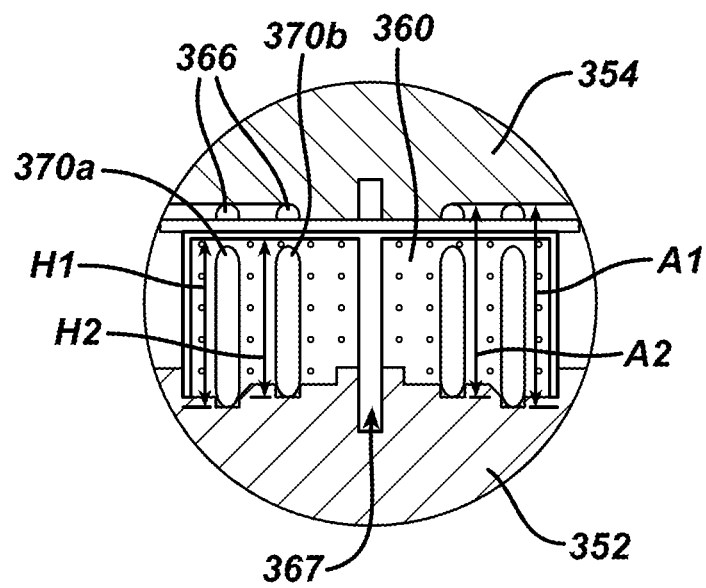
FIG. 11 is a cross-sectional view of the end effector of FIG. 9.

In some embodiments, staples contained within a staple cartridge of an end effector can be configured to create a desired compression profile within tissue captured by the staples. The desired compression profile can be created in stapled tissue, for example, where staples within the staple cartridge have different unformed staple heights. As shown in FIG. 10, an unformed height H of the exemplary staple 70 can be measured from a base 74 of the staple 70 to a top, or tip, of legs 72a, 72b of the staple 70. Referring now to FIG. 11, which illustrates a cross section of the end effector 350, a first group of staples 370a can have first staple height H1 that is taller than a second staple height H2 of a second group of staples 370b. The first group of the staples 370a can be positioned in a first portion of the staple cartridge 360, for example in an outer portion, and the second group of staples 370b can be positioned in a second portion of the staple cartridge 360, for example in an inner portion. In the illustrated embodiment, the cartridge 360, and therefore the compression gradient, can be configured to be symmetrical about a slot 367 configured to receive a cutting instrument, e.g., the E-beam 86, therethrough. It will be appreciated by a person skilled in the art that the first and second groups of staples 370a, 370b can be arranged in any pattern and can be spaced laterally and/or longitudinally along the cartridge 360. In certain embodiments, a plurality of staple groups, each group having different unformed staple heights, can be utilized. In at least one such embodiment, a third group having an intermediate staple height can be positioned in the cartridge intermediate the first group of staples and the second group of staples. In various embodiments, each staple within a staple row in the staple cartridge can comprise a different staple height. In at least one embodiment, the tallest staple within a staple row can be positioned on a first end of a staple row and the shortest staple can be positioned on an opposite end of the staple row. In at least one such embodiment, the staples positioned intermediate the tallest staple and the shortest staple can be arranged such that the staple heights descend between the tallest staple and the shortest staple, for example.

Figure 12:
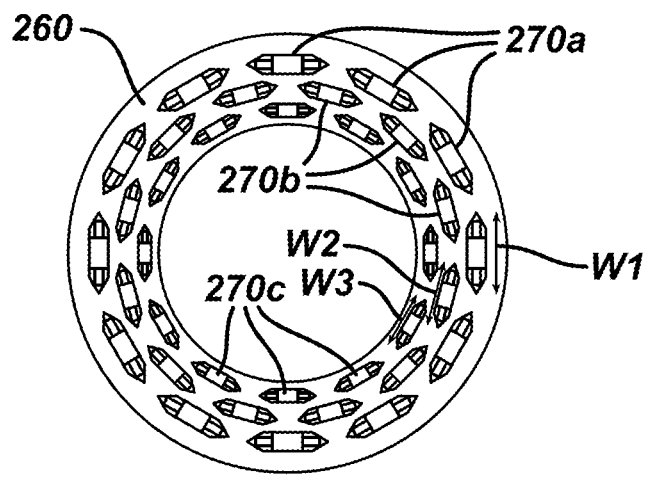
FIG. 12 is a top view of a prior art staple cartridge for use with the instrument of FIG. 7.

Similarly, staples within a staple cartridge can have different crown widths to create a desired compression profile in the stapled tissue. As shown in FIG. 10, a crown width W of the exemplary staple 70 can be measured from one side of the base 74 of the staple 70 to an opposite side. Like the above-described variations in staple height H, variations in the staple width W can be spaced throughout the staple cartridge to create a plurality of staple groups dispersed longitudinally and/or laterally across the cartridge. By way of non-limiting example, FIG. 12 illustrates a staple cartridge 260 for use with the surgical instrument 200 and having staples 270 therein with different crown widths W. The staple cartridge 260 houses three groups of staples 270a, 270b, 270c, each having different widths W1, W2, and W3, respectively, although any number of staple groups is possible. As shown, the groups of staples 270a, 270b, 270c can be arranged in circumferential rows, with the staples 270c having the largest width W1 positioned on an outermost edge of the cartridge 260 and the staples 270a having the smallest width W3 positioned on an innermost edge of the cartridge 260. In other embodiments, staples having a larger crown width can be positioned near an inner most edge of a cartridge and staples having a smaller crown width can be positioned near an outer edge of the cartridge. In still further embodiments, staples along the same row can have different crown widths.

Figure 13:
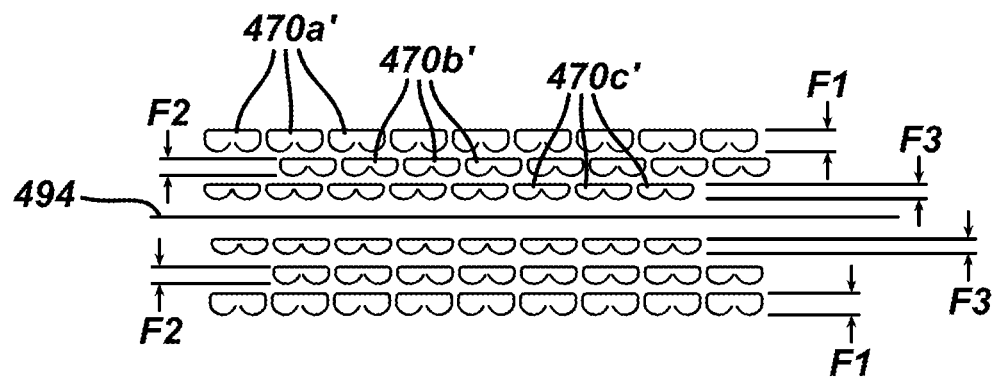
FIG. 13 is a diagrammatic representation of lines of staples installed using a prior art surgical stapling instrument.

Additionally or alternatively, it may be possible to create a desired tissue compression profile by the creation of different formed (final) staple heights. FIG. 13 illustrates an exemplary embodiment of lines of formed staples 470' installed using a surgical stapling instrument as described herein and configured to apply staples 470' having different formed heights as well as to cut tissue to thereby create a cut line 494. As shown in FIG. 13, formed heights F1 of a first group of staples 470a' in a first row that is the farthest distance away from the cut line 494 are greater than formed heights F3 of a third group of staples 470c' in a third row that is closest to the cut line 494. A second group of staples 470b' in a second row that is formed between the first and third rows can have staples 470b' with a formed height F2 that is between the heights F1, F3. In other embodiments, formed heights of the staples can decrease from an innermost row to an outermost row. In still further embodiments, formed heights of the staples in a single row can increase or decrease from staple to staple.

Referring again to FIG. 11, differences in formed staple heights can be attained by, for example, altering a staple forming distance A. Forming distances A1, A2 can be measured from a seat of staples 370a, 370b, respectively, within the cartridge 360, and an apex of a corresponding forming pocket 366 of the anvil surface 358 when the upper jaw 354 is in the closed position. In one embodiment, for example, a first staple forming distance A1 is different from a second staple forming distance A2. Because the forming distance A1 is greater than the forming distance A2, the staples 370a are not compressed as much as the staples 370b, which can alter the formed heights of the staples 370a, 370b. In particular, greater amounts of compression, corresponding to smaller forming distances, can result in staples with smaller formed (final) heights. It will be understood that similar results may be attained in any desired pattern.

Figure 14:
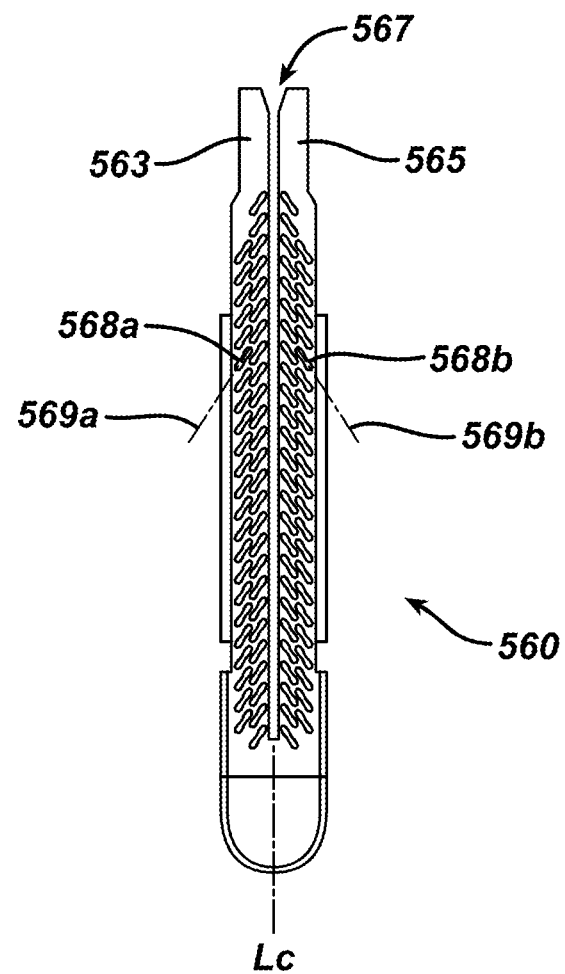
FIG. 14 is a top view of a prior art staple cartridge having a staple pattern.
Figure 15A:
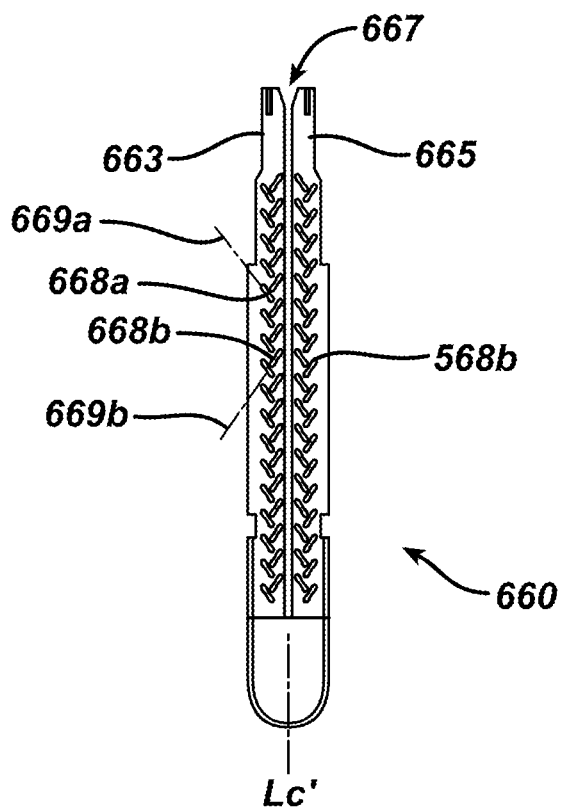
FIG. 15A is a side view of an end effector with a staple cartridge loaded with an adjunct material.

Varied tissue compression gradients can be obtained via patterns in staple orientation within a staple cartridge, for example by the patterns illustrated in FIGS. 14 and 15A. In the embodiment depicted in FIG. 14, staple cartridge 560 can include at least one first staple cavity 568a and at least one second staple cavity 568b for housing staples 570 therein. The first cavity 568a can be situated on first lateral side 563 of the cartridge 560 and the second cavity 568b can be situated on a second lateral side 565 of the cartridge 560, the first and second lateral sides 563, 565 being separated by a slot 567 configured to receive a cutting instrument, e.g., the E-beam 86, therethrough. The first cavity 568a can define a first longitudinal axis 569a and the second cavity 568b can define a second longitudinal axis 569b. In the illustrated embodiment, the first axis 569a is perpendicular, or substantially perpendicular, to the second axis 569b. In other embodiments, the first axis 569a can be transverse to the second axis 569b such that axes 569a, 569b can create an acute or obtuse angle therebetween. In still other embodiments, the first axis 569a can be parallel to, or substantially parallel to, the second axis 569b. In some embodiments, at least a portion of the staple cavities 568a, 568b can overlap, such that staples 570 therein can be interlocked when formed. The cartridge 560 can have a plurality of each of the first and second cavities 568a, 568b, which can be arranged in any pattern on first and second sides 563, 565 of the cartridge 560, for example in rows extending along both sides 563, 565 of the cartridge 560 along a longitudinal axis Lc of the cartridge 560. The staples 570 housed within the cavities 568a, 568b can be implanted into tissue in a pattern determined by the orientation and positioning of the cavities 568a, 568b. The cartridge 560, for example, can be used to implant staples 570 having different orientations of the staples 570 on opposite sides of an incision line created by a surgical instrument carrying the cartridge 560.

In other embodiments, for example the embodiment of a cartridge 660 illustrated in FIG. 15A, staple cavities 668a and 668b having different orientations can both be disposed on a single lateral side of the cartridge 660. As shown in FIG. 15A, an axis 669a of the first staple cavity 668a is perpendicular, or substantially perpendicular, to an axis 669b of the second staple cavity 668b, both of which are disposed on each of first and second lateral sides 663, 665 of the cartridge 660. In other embodiments, the axes 669a, 669b can form an acute or obtuse angle therebetween, or can be parallel to one another. A plurality of the first and second cavities 668a, 668b can be aligned in adjacent rows along a longitudinal axis Lc' of the cartridge 660 on each of the first and second sides 663, 665 of the cartridge 660. In this embodiment, staples 670 housed within the cavities 668a, 668b can be implanted into tissue in a symmetrical pattern about an incision line created by a surgical instrument carrying the cartridge 660. Greater detail on staple patterns, as well as additional embodiments of such patterns, can be found in U.S. Publication No. 2011/0192882, incorporated herein by reference in its entirety.

Exemplary Compositions for Adjunct Materials

Figure 15B:
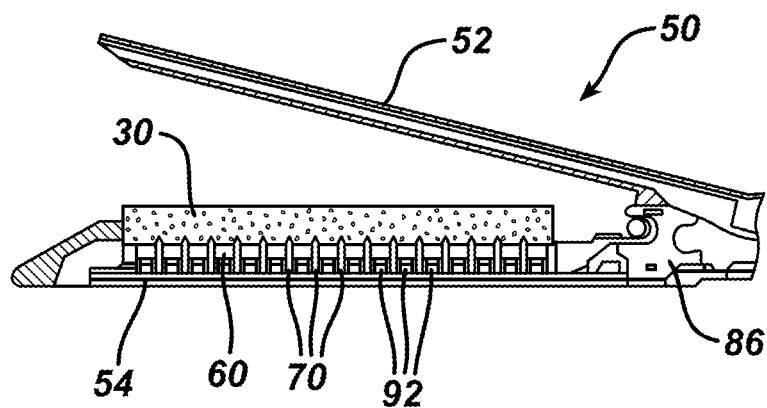
FIG. 15B is a side, cross-sectional view of the end effector of FIG. 4 having an adjunct material thereon.

Regardless of the configuration of the surgical instrument, the present disclosure provides for the use of implantable materials, e.g., synthetic and/or biological materials, collectively "adjunct materials," in conjunction with instrument operations. As shown in FIG. 15B, the end effector 50 can include at least one piece of adjunct material 30 positioned intermediate the lower and upper jaw members 52, 54 and it can be releasably retained to one of the staple channel 56 and/or the anvil surface 58. In use, the adjunct material 30 and patient tissue can be captured by staples 70 when the staples 70 are fired. Then, the adjunct material 30 can be separated from the surgical stapler and can remain in the patient when the stapler is removed from the patient. Exemplary devices and methods for attaching one or more adjunct materials to an end effector of a surgical instrument can be found in U.S. Publication No. 2013/0256377 and U.S. Publication No. 2013/0153641, incorporated herein by reference in their entirety.

Adjunct material used in conjunction with the disclosures provided for herein can have any number of configurations and properties. Generally, they can be made from a bioabsorbable material, a biofragmentable material, and/or a material otherwise capable of being broken down, for example, such that the adjunct material can be absorbed, dissolved, fragmented, and/or broken down during the healing process. In at least one embodiment, the adjunct material can be configured to degrade over time to form a gel, e.g., a sealant, to assist in wound healing. In other embodiments, the adjunct material can include a therapeutic drug that can be configured to be released over time to aid the tissue in healing, for example. In further various embodiments, the adjunct materials can include a non-absorbable and/or a material not capable of being broken down, for example.

Some particularly advantageous adjunct materials can include porous polymer scaffolds that can be configured to be broken down, for example by exposure to water such that the water attacks the linkage of a polymer of the material. The degraded material can be configured to gel over a wound site to thereby coat the wounded tissue, e.g., wounded soft tissue, which can aid in compressing, sealing and/or generally creating an environment at the wound site that promotes healing of the tissue. In particular, such degradable polymers can allow for the tissue itself to become the weight-bearing component. In some embodiments, the degraded material can include chemoattractant agents that attract natural healing compounds to the wound site. The polymer scaffolds can be configured to have a desired rate of degradation, for example within minutes to hours after attachment to tissue, to thereby assist in the healing process almost immediately after attachment. For more details on porous polymer scaffolds as described herein, see Q. Chen et al., Elastomeric biomaterials for tissue engineering, Progress in Polymer Science 38 (2013) 584-671, incorporated herein by reference in its entirety.

In some embodiments, the porous polymer scaffolds described herein can be physically crosslinked, which can allow for shaping of the polymer into various complicated three-dimensional shapes, e.g., fibers, sheets, films etc., having any desired porosity, surface-to-volume ratio, and mechanical properties. The scaffold can be shaped into a desired form via a number of methods, for example by extrusion, wet spinning, electrospinning, thermally induced phase separation (TIPS), salt leaching/freeze-drying, etc. Where the scaffold is formed into a film or sheet, the film or sheet can have any desired thickness, for example in a range of about 50 to 750 µm or in a range of about 1 to 3 mm, depending on the desired application.

One embodiment of a porous polymer scaffold includes multiple layers, each of which can perform different wound healing functions. In an exemplary embodiment, the scaffold includes three layers. The first layer can be made from polyester carbonate urethane urea (PECUU), the second layer can be made from poly(ester urethane) urea (PEUU), and the third layer can be made from poly(carbonate urethane) urea (PCUU) lysine triisocyanate (LTI) or hexamethylene diisocyanate (HDI). A person skilled in the art will appreciate that the properties of each layer can be optimized to achieve desired results and performance. In some embodiments, the desired properties of the scaffold can be achieved by blending or copolymerizing the material of the third layer or copolymerized with various polymers or copolymers. By way of non-limiting examples, the material of the third layer can be blended with a polyester copolymer, for example polycaprolactone (PCL), polyglycolic acid PGA, poly(D,L-lactic acid) (PDLLA), PGA, and/or polyethylene glycol (PEG). Where the material of the third layer is blended with both the polyester copolymer and the PEG, a ratio of the polyester to the PEG in the third layer can be about 50:50. In another exemplary embodiment, the PCL can be present in a range of about 60-70% weight/volume, the PGA can be present in a range of about 20-30% weight/volume, the PEG can be present in a range of about 50% weight/volume, and the PDLLA can be present in a range of about 10% weight/volume.

The three-layered film can be configured to degrade almost immediately upon attachment to tissue, for example within about 1 to 2 hours after attachment, although each of the three layers can be configured to degrade differently to have different healing benefits. The order, number, and thickness of each of the layers can vary, and can be tailored to create desired degradation and/or compression ratios. In some embodiments, the first, second, and third layers can be formed on top of a base material or substrate, for example on top of PCL, which can be configured to aid in mechanical compression of the wounded tissue.

Another exemplary embodiment of a porous polymer scaffold can be synthesized from polyhydroxyalkanoate (PHA). In an exemplary embodiment, the PHA can be naturally produced from a variety of microorganisms, e.g., Gram-negative or Gram-positive bacteria, or it can be synthesized, e.g., similar to the production of Biopol®, available from Zeneca of London, United Kingdom. Because PHAs are very quick to dissolve, scaffolds made from PHA can begin to degrade within 20 to 30 minutes after attachment to tissue via contact with heat and/or water. Where the PHA scaffold has a higher molecular weight, the degradation time can be higher, for example in a range of about 30 minutes to about 10 hours. The PHA can be formed into a very thin film, for example a film having a thickness of less than 0.1 mm, e.g., in a range of between 50 to 750 µm. In some embodiments, the PHA can be copolymerized and/or blended with one or more additional materials. By way of non-limiting example, the PHA can be copolymerized with hydroxlvalerate (HV), hydroxylbutyrate (HB), and/or hydroxylhexanoate (HH), which can reduce a level or crystallinity and/or brittleness of the PHA. In other embodiments, the PHA can be blended with one or more thermoplastics, e.g., poly(lactic acid) (PLA), PGA, PCL, starch, etc., to thereby customize a molecular weight and resultant mechanical properties of the scaffold. In certain aspects, one or more of the polymers can be a thermoplastic polymer.

In other embodiments, the scaffold can be synthesized from poly(polyol sebacate) (PPS), e.g., from poly(glycerol-sebacate) (PGS). Such scaffolds can be particularly biocompatible and can provide an additional advantage of reducing a risk of infection in addition to promoting healing. Other exemplary embodiments can be synthesized from xylitol-based elastomers, for example polyxylitol sebacates (PXSs), which can offer structural stability over a clinically required period and/or can enter the metabolic pathway slowly without causing rapid fluctuations of blood glucose levels. Scaffolds made from PXS's can be formed into a thicker film to thereby provide greater compression to the wound site, and can be configured to degrade within a range of about 10 hours to 8 days after attachment. Still other exemplary embodiments can be synthesized from poly(glycerol sebacate-co-acrylate) (PGSA), which can promote tissue ingrowth into the scaffold, particularly when formed as a fiber, and/or can serve as an antibacterial agent. PGSA scaffolds can be useful as a replacement for traditional surgical sutures and staples, and/or can serve as a waterproof sealant for hollow organ anastomoses (e.g., ducts, intestine, etc.), 2D mesh grafts (e.g., treatment of hernias, ulcers, burns, etc.), and/or wound dressings (e.g., hemostatic patches, etc.). The PGSA can be combined with glycerol, which can allow the scaffold to last longer in situ, for example up to 20 days.

In yet another embodiment, the scaffold can be made from poly($\epsilon$-caprolactone) (PCL), which can be blended with silk fibroin (SF) and which can be formed into a very thin film. The PCL/SF blend can have highly biocompatible properties and/or can improve cell attachment and/or proliferation to the scaffold. For example, when implanted onto tissue, the scaffold can release fibroin into the tissue to thereby promote faster healing, nearly immediate hemostasis, and/or to attract fibroblasts in greater numbers. The PCL component can further assist in the healing process by providing mechanical compression of the wounded tissue. A higher PCL content can provide better mechanical properties, while a higher SF content can provide better degradation properties. In general, the PCL content can be in a range of about 50 to 90% weight/volume and the SF content can be in a range of about 10 to 50% weight/volume. More details on the properties and manufacturing methods for scaffolds made from PCL and SF can be found in Jun Sik Lim et al., Fabrication and Evaluation of Poly(epsilon-caprolactone)/Silk Fibroin Blend Nanofibrous Scaffold, Biopolymers 97: 265-275 (2012), incorporated herein by reference in its entirety.

In still further embodiments, the scaffold can include PCL coated with a gelatin. The scaffold can be arranged in one or more layers, for example with the PCL serving as a substrate. The PCL can function to increase a mechanical strength of the scaffold and/or can support fibroblast adhesion and cell proliferation. More details on the properties and manufacturing methods for scaffolds made from gelatin-coated PCL can be found in Pengcheng Zhao et al., Biodegradable fibrous scaffolds composed of gelatin coated poly ($\epsilon$-caprolactone) prepared by coaxial electrospinning, J. Biomed Mater Res 83A: 372-382 (2007), incorporated herein by reference in its entirety.

Table 1 below outlines exemplary molecular weight ranges, approximate absorption times, and average dimensions of films made from the aforementioned porous polymer scaffold materials. It will be appreciated by a person skilled in the art that the ranges provided in Table 1 are not intended to be limiting, and that a molecular weight of any of the polymers described herein can be altered to obtain the desired degradation properties.

TABLE 1

| Film | Average molecular weight in Daltons | Approximate absorption times | Average thickness | Average length | Average width |
|---|---|---|---|---|---|
| Polyester carbonate urethane urea (PECUU) | 5,000 to 80,000 | 14 to 60 days | 10 μm to 1 mil | 25.4 to 100 mm | 10.3 to 12.7 mm |
| Poly(ester urethane)urea (PEUU) | 5,000 to 80,000 | 14 to 60 days | 10 μm to 1 mil | 25.4 to 100 mm | 10.3 to 12.7 mm |
| Poly(carbonate urethane)urea (PCUU) | 10,000 to 200,000 (preferably 15,000 to 50,000) | 14 to 60 days | 100 μm to 1 mil | 25.4 to 100 mm | 10.3 to 12.7 mm |
| Polyhydroxyalkanoate (PHA) | $2.107 \times 10^{29}$ to $2.589 \times 10^{29}$ | 7 to 60 days | 100 μm to 1 mil | 25.4 to 100 mm | 10.3 to 12.7 mm |
| Poly(polyol sebacate) (PPS) | 89,000 and 124,000 | 7 to 60 days | 100 μm to 1 mil | 25.4 to 100 mm | 10.3 to 12.7 mm |
| Polyxylitol sebacates (PXS's) | $1.47 \times 10^{27}$ to $3.73 \times 10^{27}$ | 7 to 60 days | 100 μm to 1 mil | 25.4 to 100 mm | 10.3 to 12.7 mm |
| Poly(glycerol sebacate-co-acrylate) (PGSA) | $5.8 \times 10^{26}$ to $7.5 \times 10^{26}$ | 7 to 60 days | 10 μm to 1 mil | 25.4 to 100 mm | 10.3 to 12.7 mm |
| Poly($\epsilon$-caprolactone); silk fibroin; scaffold (PCL/SF) Blend PCL/SF (50/50) | 25,000 to 325,000 (SF) $4.21 \times 10^{28}$ to $4.81 \times 10^{28}$ (PCL) | 21 to 60 days (SF) 2 to 3 years (PCL) | 10 μm to 1 mil | 25.4 to 100 mm | 10.3 to 12.7 mm |
| Gelatin coated PCL (poly ($\epsilon$-caprolactone) | $3.01 \times 10^{28}$ to $1.98 \times 10^{29}$ (gelatin) $4.21 \times 10^{28}$ to $4.81 \times 10^{28}$ (PCL) | 7 days (gelatin) 2 to 3 years (PCL) | 100 μm to 1 mil | 25.4 to 100 mm | 10.3 to 12.7 mm |

Other suitable adjunct materials can include absorbable polyurethanes, e.g., polyurethanes derived from aromatic absorbable isocyanates that can be similar to methylene bis(phenyl isocyanate) (MDI) and chain extender diols. The absorbable polyurethanes can be configured to hydrolytically degrade into safe and biocompatible products upon hydrolysis. Non-limiting examples of hydrolysable aromatic isocyanates that can be used to form the absorbable polyurethanes include glycolate-diisocyanate, caprolactone-diisocyanate, glycolate-ethylene glycol-glycolate, glycolate-diethylene glycol-glycolate, lactate-diethylene glycol-lactate, trimester of gycolic acid with trimethylpropane, and tetraester of glycolic acid with pentaerythritol.

Another particularly advantageous adjunct material that can be used in conjunction with the disclosures provided herein are the materials that form the multilayered dressings disclosed in U.S. Publication No. 2006/0257458, incorporated herein in its entirety, which are particularly suited to absorb and retain fluids when compressed, e.g., by the application of staples. Other exemplary, non-limiting examples of synthetic materials that can be used in conjunction with the disclosures provided for herein, e.g., as a buttress, include biodegradable synthetic absorbable polymer such as a polydioxanon film sold under the trademark PDS® or with a Polyglycerol sebacate (PGS) film or other biodegradable films formed from PGA (Polyglycolic acid and various forms thereof, marketed under the trademarks Vicryl, Dexon, and/or Neoveil), PCL (Polycaprolactone), PLA or PLLA (Polylactic acid), PHA (polyhydroxyalkanoate), PGCL (poliglecaprone 25, sold under the trademark Monocryl), PANACRYL (Ethicon, Inc., Somerville, N.J.), Polyglactin 910, Poly glyconate, PGA/TMC (polyglycolide-trimethylene carbonate sold under the trademark Biosyn), polyhydroxybutyrate (PHB), poly(vinylpyrrolidone) (PVP), poly(vinyl alcohol) (PVA), polydioxanone (PDO) and various forms thereof (e.g., marketed under the trademark PDS) or a blend or copolymerization of any of the above. Blends and/or copolymerizations of any of the aforementioned materials can be tailored to have a desired molecular weight and/or degradation rate.

Some non-limiting examples of biologic derived materials that can be used in conjunction with the disclosures provided for herein, e.g., as a sealant material, include platelet poor plasma (PPP), platelet rich plasma (PRP), starch, chitosan, alginate, fibrin, thrombin, polysaccharide, cellulose, collagen, bovine collagen, bovine pericardium, gelatin-resorcin-formalin adhesive, oxidized regenerated cellulose, regenerated cellulose, mussel-based adhesive, poly (amino acid), agarose, polyetheretherketones, amylose, hyaluronan, hyaluronic acid, whey protein, cellulose gum, starch, gelatin, silk, Progel®, available from Davol Inc. of Warwick, R.I., TachoSil®, available from Baxter of Deerfield, Ill., or other material suitable to be mixed with biological material and introduced to a wound or defect site, including combinations of materials, or any material apparent to those skilled in the art in view of the disclosures provided for herein. Biologic materials can be derived from a number of sources, including from the patient in which the biologic material is to be implanted, a person that is not the patient in which the biologic material is to be implanted, or other animals.

Additional disclosures pertaining to synthetic or polymer materials and biologic materials that can be used in conjunction with the disclosures provided herein can be found in U.S. Pat. No. 7,772,352, PCT Publication No. WO 2014/016819, U.S. Patent Application Publication No. 2006/0257458, U.S. Patent Application Publication No. 2012/0080335, U.S. Patent Application Publication No. 2012/0083835, U.S. Patent Application Publication No. 2013/0256372, U.S. Patent Application Publication No. 2013/0256365, U.S. Patent Application Publication No. 2013/0256376, U.S. patent application Ser. No. 13/710,931, entitled "Electrosurgical End Effector with Tissue Tacking Features," and filed on Dec. 11, 2012, and U.S. patent application Ser. No. 13/763,192, entitled "Multiple Thickness Implantable Layers for Surgical Stapling Devices," and filed on Feb. 8, 2013, each of which is incorporated by reference herein in its entirety.

Woven Adjunct Materials

Adjunct materials are provided for sealing of a staple line against fluid leakage. One advantage of tissue adjuncts is their propensity to prevent or minimize leaks, such as fluid or gas leaks. Tissue adjuncts can perform this function by one or more of the following mechanisms: plugging holes or tears that occur at the staple puncture sites; restricting movement of tissue around staple puncture sites to prevent an increase in the size of staple holes and/or to prevent tissue tears; and minimizing strain gradients that occur between constrained tissues within the staple line and free tissue adjacent to the staple line.

A woven adjunct material can provide reinforcement to the staple line and can prevent tears in the tissue or pulling of the staples through the tissue by distributing stress along the tissue near a staple line. Further, a woven adjunct material can absorb impact from stapling and reduce trauma at and/or beyond the staple line. In certain aspects, the woven adjunct material can act as a medium into which staples can penetrate into when tissue at the staple site is thin or diseased. A woven adjunct material can thus be configured to both distribute the compressive load and to compensate for variable tissue thickness. In certain aspects, an adjunct material can include a plurality of layers, at least one of which is woven, such as a core and one or more layers. A size, shape, and a composition of the material forming each these layers can be selected in various ways to influence mechanical properties of the resulting adjunct material, such as a compressibility and fluid absorption capability of the adjunct.

An adjunct material can be inserted into a patient and deployed at a surgical site in various ways. For example, an adjunct material can be releasably coupled to an end effector of a surgical stapler, the end effector including a cartridge assembly and an anvil. When the end effector is positioned adjacent to a surgical site, tissue can be engaged between the cartridge assembly and the anvil. Actuation of the surgical stapler can eject staples from the cartridge assembly, through the adjunct material, and into the tissue grasped between the jaws. The adjunct material can help to reduce trauma from the stapling and distribute stress load across the tissue near the staple line to reduce a likelihood that the tissue will tear. In certain aspects, the adjunct material can elute a therapeutic agent, serve to absorb fluid, adjust for variations in material thickness, or perform various other functions when the adjunct is deployed onto tissue.

A woven adjunct material can have various sizes, shapes, and configurations. In one embodiment, a woven adjunct material includes an inner core layer and at least one outer layer of material. The outer layer of material can be positioned on one or more sides of the core layer, e.g., top, bottom, and/or lateral sides of the core layer. In one embodiment, a flexible support layer can surround all sides of the elastic core layer so as to envelop the elastic core. The core layer and flexible support layers can be formed from various materials. For example, the elastic core layer can be a layer of loosely woven material, and a tightly woven material can surround the elastic core layer on at least one side and can act as a flexible support layer. Each of the flexible support layers can include fibers 3004, which can be the same as or different than fibers 3005 in the elastic core layer 3003. FIG.

16B illustrates one exemplary embodiment of a woven adjunct material 3000 in which flexible support layers 3001, 3002, are positioned on the top and bottom of the elastic core layer 3003, respectively.

Figure 16A:
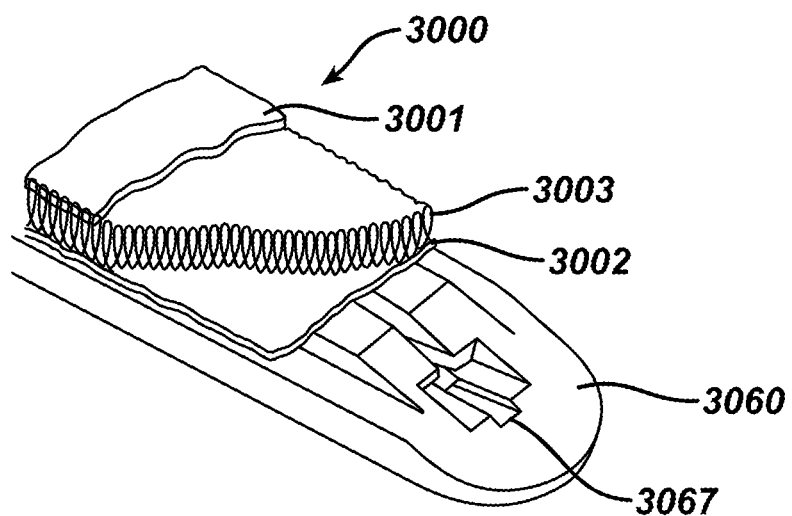
FIG. 16A is a perspective view of a woven adjunct material loaded onto a cartridge assembly of a surgical stapler.

The woven adjunct material can be configured to releasably couple to an end effector of a surgical instrument, such as a cartridge assembly and/or anvil of a surgical stapler. For example, FIG. 16A shows the woven adjunct 3000 including the two flexible support layers 3001, 3002 on the top and bottom of the elastic core layer 3003 and coupled to a cartridge assembly 3060 having a knife slot 3067 and a plurality of staple cavities (not shown). The woven adjunct can be releasably retained on any of the end effectors of the surgical staplers provided herein e.g., staplers 10, 100, 200, an open linear cutting stapler.

The adjunct material can deliver various benefits to the tissue when the adjunct material is stapled to the tissue. FIG. 16C shows the effects of an adjunct material A on a tissue T. As illustrated in FIG. 16C, the adjunct material A can compensate for variable thickness of the tissue at the staples S by compressing under the load of the staples S. The adjunct material A can distribute a strain on the tissue T from the staples S to a portion of the tissue T positioned beyond the staple line to prevent tearing along the tissue T at or beyond the staple line.

FIGS. 17A-C show a behavior of an adjunct material 3000 when a compressive force is applied and then released. More specifically, FIG. 17A shows the adjunct material 3000 before application of a compressive force. FIG. 17B shows the adjunct material 3000 having a compressive force applied thereto which decreases a thickness of the adjunct. FIG. 17C shows the adjunct material 3000 after the compressive force is released therefrom, which increases a thickness of the adjunct. This compression and expansion capability can result from the structure of the adjunct material.

The support layer(s) of the woven material 3000 can be formed in a variety of weave patterns and geometries to provide desired mechanical properties, such as flexibility, pressure distribution, homeostasis, and pneumostasis. The weave pattern used to form support layer(s) can vary and can include, by way of non-limiting example, those achieved by flat knitting processes with various needles, circular knitting processes with various needles, double knitting, warp knits, weft, knits, plain weaves, pile weaves, etc. The flexible support layer 3001, 3002 and the elastic core layer 3003 can have the same weave pattern or the flexible support layer and the elastic core layer can have different weave patterns to achieve a desired property for each layer. Additional processes can be applied to a layer to adjust its size, density, mechanical properties, surface properties, appearance, etc. These processes include the application of heat, the application of heat under a boundary condition such as force or displacement, a chemical treatment (e.g., scouring, mercerizing, singeing, raising, calendaring, sanforizing, etc.). A person of skill in the art will appreciate that the structure of the flexible support layer(s) of the woven adjunct can be adjusted to achieve desired properties. For example, the flexible support layer(s) can have a tighter weave than a weave of the core layer. In certain aspects, the flexible support layer(s) can be densely woven. Regarding a relative density of the support layer and the core layer, the support layer(s) can be in the range of about 2 to 10 times more densely woven than the elastic core layer.

Figure 16B:
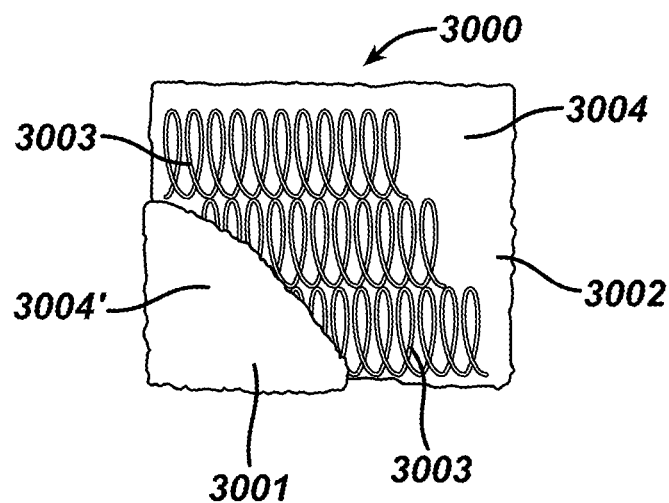
FIG. 16B is a top view of the woven adjunct material of FIG. 16A.
Figure 16C:
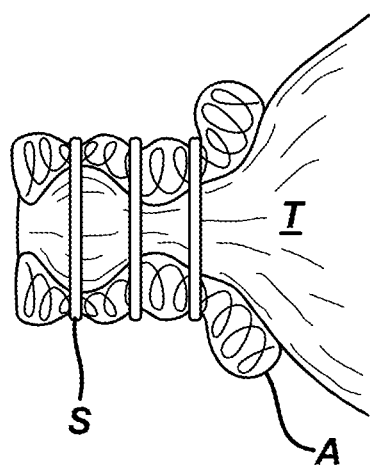
FIG. 16C is a side view of the woven adjunct material of FIG. 16A stapled onto tissue.
Figure 18:
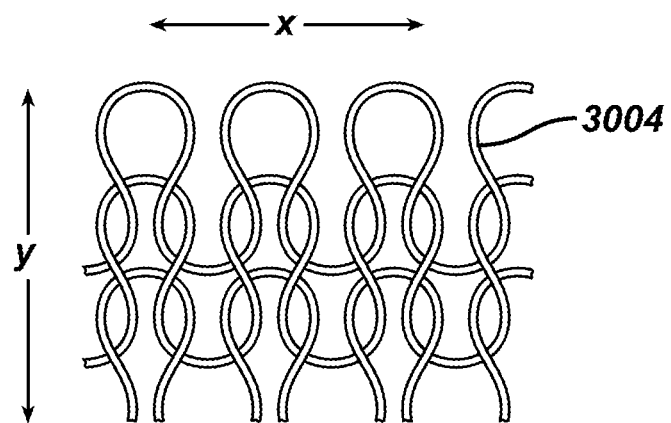
FIG. 18 is a side view of one embodiment of a woven structure.

FIG. 18 illustrates an exemplary weave of fibers used to form the support layers 3001, 3002 of FIGS. 16A-16C. As shown, fibers 3004 can be woven into loops which interlock in both the X and Y directions. A weave density of the flexible support layers 3001, 3002 can be sufficiently dense so that the support layers 3001, 3002 are not transparent to light. The weave density can be characterized in various ways, such as by a degree of binding between adjacent fibers. The fibers can be interlocked, as shown, or knotted together, such that there is substantially no relative motion between the fibers when a force is applied to the layer. Fibers 3004 may be comprised of a braided mix of multiple smaller fibers made of one or more materials. The selection or materials, fiber diameter, and ratios of different fiber constituents (e.g., five fibers of a first material for every one fiber of a second material) can impact the behavior of fibers 3004.

One skilled in the art will appreciate that the flexible support layer(s) 3001, 3002 can be formed from various types of fibers that are biocompatible and bioabsorbable. Examples of such materials include various materials from which sutures are made, including naturally occurring fiber materials and synthetic fibers. Exemplary materials include polydioxanon (sold under the trademark PDS®), Polyglycerol sebacate (PGS), PGA (Polyglycolic acid and various forms thereof, marketed under the trademarks VICRYL® and/or NEOVEIL®), PCL (Polycaprolactone), PLA or PLLA (Polylactic acid), PHA (Polyhydroxyalkanoate), PGCL (Poliglecaprone 25, sold under the trademark MONOCRYL®, PANACRYL® (Ethicon, Inc., Somerville, N.J.), polyglactin 910, polyglyconate, PGA/TMC (polyglocolide-trimethylene carbonate sold under the trademark BIOSYN®), polyhydroxybutyrate (PHB), poly(vinylpyrrolidone) (PVP), poly(vinyl alcohol) (PVA), absorbable polyurethanes, regenerated cellulose, and oxidized regenerated cellulose fibers (ORC). Blends and/or copolymerizations of any of the aforementioned materials can be tailored to have a desired molecular weight, mechanical properties, and/or degradation rate. In one embodiment, the flexible support layers(s) 3001, 3002 can be formed as a non-woven structure derived from the aforementioned materials. These materials may be in the form of a foam and/or film. In one embodiment, the flexible support layers(s) are at least partially comprised of PDS® to facilitate adherence to elastic core layer 3003. In one embodiment, fiber 3004 is a braided filament comprised of five Vicryl® fibers and one PDS® fiber.

In one embodiment, the flexible support layer(s) 3001, 3002 can be formed from a combination of synthetic fibers and naturally occurring fibers. For example, a naturally occurring fiber or fibers can be woven into the tissue contacting surface of a flexible support layer primarily comprising synthetic fibers. Exemplary naturally occurring materials include oxidized regenerated cellulose fibers (ORC) and regenerated cellulose. The naturally occurring material, particularly ORC, can be advantageous as it can function to form a seal with the tissue as it tends to gelatinize upon contact with a liquid.

A size of the fibers in the flexible support layer(s) can be selected to achieve desired mechanical properties. An exemplary composition of the flexible support layer is fibers 3004 in the support layer(s) can be in the range of about 10-0 to 24-0 in size, i.e., about 0.024 mm to 0.3 mm. In addition, the fibers of the flexible support layer(s) can be of various fiber types including monofilament and braided.

The elastic core layer 3003 can have various sizes, shapes, and configurations, and the material of the elastic core layer can be selected to achieve desired mechanical properties. The elastic core layer 3003 can include a knitted or woven structure that is loose in one direction (the direction of deformation) that readily compress when a compressive force is applied and then can expand when the compressive force is no longer applied. Increasing resistance to compression (in the direction of deformation) can be achieved by compacting the structure in the plane perpendicular to the direction of primary deformation. This compact structure can be achieved by post-knitting process steps such as heating, mechanical compression, etc. Further, the fibers in the elastic core layer can be loosely woven such that the fibers are able to move relative to one another more readily than the interlocked or knotted fibers in the support layer. As such, the weave density of the elastic core layer 3003 is typically significantly less dense in at least one direction than that of the support layers 3001, 3002. By way of example, the relatively low weave density of the elastic core layer 3003 can be characterized in terms of the weave density being sufficiently low so as to permit it to be transparent to light. An alternative description would be a deformation inducing a stretch ratio of approximately 0.5 requires a pressure of approximately 3 g/mm².

Like the flexible support layer(s), the elastic core layer can be formed from various types of fibers that are biocompatible and bioabsorbable. Examples of such materials include various materials from which sutures are made, including naturally occurring fiberous materials and synthetic fibers. Exemplary materials include polydioxanon (sold under the trademark PDS®), Polyglycerol sebacate (PGS), PGA (Polyglycolic acid and various forms thereof, marketed under the trademarks VICRYL® and/or NEOVEIL®), PCL (Polycaprolactone), PLA or PLLA (Polylactic acid), PHA (Polyhydroxyalkanoate), PGCL (Poliglecaprone 25, sold under the trademark MONOCRYL®, PANACRYL® (Ethicon, Inc., Somerville, N.J.), polyglactin 910, polyglyconate, PGA/TMC (polyglocolide-trimethylene carbonate sold under the trademark BIOSYN®), polyhydroxybutyrate (PHB), poly(vinylpyrrolidone) (PVP), poly (vinyl alcohol) (PVA), absorbable polyurethanes, regenerated cellulose, and oxidized regenerated cellulose fibers (ORC). Blends and/or copolymerizations of any of the aforementioned materials can be tailored to have a desired molecular weight, mechanical properties, and/or degradation rate. In one embodiment, the elastic core layer 3003 can be at least partially comprised of PDS® to facilitate adherence to flexible support layer(s) 3001, 3002. In one embodiment, fiber 3005 is a braided filament comprised of five Vicryl® fibers and one PDS® fiber.

A size of the fibers in the elastic core layer can affect the properties of the adjunct material, such as elasticity, compressibility, and resiliency of the adjunct. In one embodiment, the fibers in the elastic core layer 3005 can have a greater diameter than the fibers in the flexible support layers 3004. The fibers of the elastic core can be braided or can be a monofilament. While a size of the fiber forming the elastic core can vary, in one embodiment the elastic core can be formed from fibers made of suture materials having a size in the range of about 10-0 to 2-0 in size, i.e., about 0.02 mm to 0.3 mm.

Figure 19A:
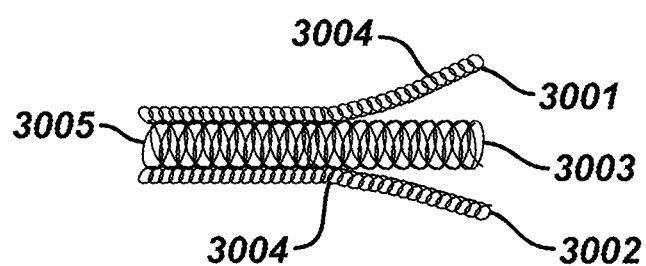
FIG. 19A is a side, cross-sectional view of a woven adjunct material having outer support layers woven onto an elastic core layer.
Figure 19B:
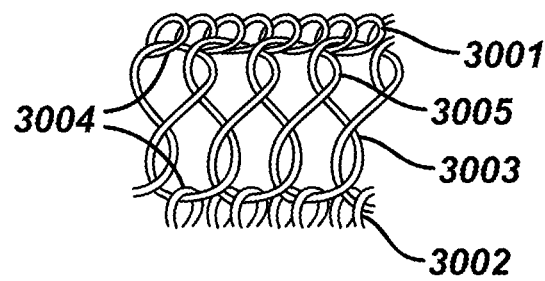
FIG. 19B is a detailed view of the woven adjunct material of FIG. 19A.

The elastic core layer and the flexible support layer(s) can be connected in various ways. For example, the elastic core layer and flexible support layer(s) can be directly connected, e.g., woven together. As shown in FIGS. 19A and 19B, the fibers 3004 of the flexible support layers 3001, 3002 can be woven around and interlocked with the fibers 3005 of the elastic core layer 3003. In another embodiment, (not shown), the elastic core and flexible support layers can be bonded together my melting one or more constituents (e.g., PDS®, etc.) comprising fibers 3004 of the flexible support layers 3001, 3002 and fibers 3005 of the elastic core layer 3003. In another embodiment (not shown), the elastic core and flexible support layers can be bonded together using any known manufacturing technique, such as using felting or otherwise adhering the layers together.

A thickness of an adjunct material, including the elastic core and the flexible support layer(s), can vary depending on the intended clinical application. In general, an adjunct material can be at least as thick as a height of a staple in its formed state. If a single adjunct material is coupled to one portion of an end effector, e.g. a cartridge assembly or an anvil, the adjunct material can be about 3.5 mm thick. Alternatively, if an adjunct material is present on both the anvil and the cartridge, each piece of adjunct material can be about one half of the height of the staple in its formed state. The flexible support layers typically have a thickness equal to about the diameter of two of the fibers used for the flexible support layer, typically from about 0.16 to 0.6 mm thick. The elastic core typically comprises the remainder of the thickness dimension of the adjunct material. Generally, the thickness of the elastic core can be in the range of about 2 to 3 mm.

Woven three-dimensional structures can be formed in such a way and using such materials that they will have desired mechanical properties. The adjunct material generally will have a number of desired properties that will vary depending upon the claimed application. One of skill in the art will understand that the material can be varied in accordance with the description above to modify these desired properties. Typically, however, when compressed and held at a height of 2 mm in a 37° C. PBS solution, the adjunct material construct can provide a minimum pressure of 3.0 gf/mm2 from the time of compression (t=0) through 72 hours. When compressed and held at a height of 2 mm in a 37° C. PBS solution, the adjunct material construct can provide pressure that does not go below the line defined by 3.0 gf/mm² @ 72 hours and 0.0 gf/mm² at day 28. When compressed to 1.0 mm, held for 15 seconds, and then released, the adjunct material can return to 2.0 mm height with at least 2.0 gf/mm² within 30 seconds. The adjunct material can be able to compress without excessive pressure to around 0.75 mm. The adjunct material should be fully reabsorbed in about 120 days.

Figure 20A:
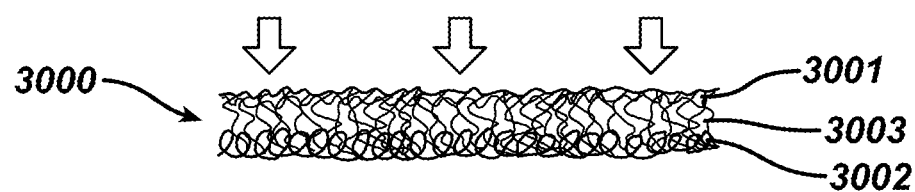
FIG. 20A is a side view of the woven adjunct material of FIG. 19A in compressed state.
Figure 20B:
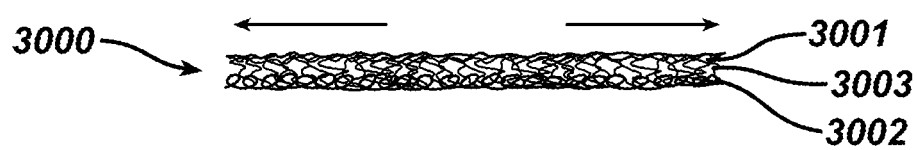
FIG. 20B is a side view of the woven adjunct material of FIG. 19A in an expanded state.

FIGS. 20A-20B show typical behavior of the adjunct material under compressive and elongation forces, respectively. FIG. 20A shows the adjunct material 3000 with a compressive force applied thereto, while FIG. 20B shows the adjunct material 3000 with an elongation force applied thereto. As shown, the adjunct material 3000 has sufficient integrity and structure such that it is not compromised by the application of these forces. The amount of material and degree of compression to be applied can determine the mechanical properties of the resultant brick. Accordingly, one of skill in the art will understand that the amount of material and degree of compression can be varied in order to modify these properties.

With the above teachings, one skilled in the art will recognize that adjunct 3000 may be comprised of one or more elastic core layers 3003 as well as one or more flexible support layers 3001, 3002. The order and number of layers as well as their orientation result in multiple combinations that are conceived within this disclosure. For example, the adjunct can include two external support layers connected by a single, central flexible layer. One skilled in the art will also appreciate that the adjunct 3000 can be formed of sandwiches of multiple flexible support layers (e.g., three layers) with a number of (e.g., two) elastic core layers.

Fibrous Adjunct Materials

In another embodiment, non-woven fibrous materials can form all or portions of an adjunct material. Like a fibrous adjunct material, the mechanical properties of a fibrous adjunct material can be influenced by the shape of the adjunct, the type of fibers used, and the density of the fibers.

The resulting material properties may also be influenced by process steps used to create the adjunct. For example, FIG. 22A illustrates an adjunct material 3100 with a central region that is more dense than regions adjacent the perimeter of the structure. FIG. 22D shows pre-processed adjunct material 3100D prior to a compressive processing step that creates adjunct material 3100. Pre-processed adjunct material 3100D is comprised of (woven or non-woven) fibers of a generally homogeneous structure and generally uniform density. By compressing the central region 3110 of 3100D to the flat height of adjunct material 3100, a central region is created that is more dense than the perimeter region.

FIG. 22B shows a wider structure 3100B being compressed to a more narrow structure (by force or by shrinkage through heat) resulting in an aligned fiber pattern with anisotropic material properties.

FIG. 22C shows a block 3100C that is pressed to increase the width resulting in an anisotropic material with an aligned fiber pattern perpendicular to that of the adjunct 3100B of FIG. 22B.

The construction of non-woven adjunct materials can be selected in various ways, but can include a fleece (e.g., a material that is similar to the fine web of cotton or wool removed by the doffing knife from the cylinder of a carding machine) and/or melt blown fibers.

A non-woven adjunct material can be formed from various types of fibers that are biocompatible and bioabsorbable. Examples of such materials include various materials from which sutures are made, including naturally occurring fiber materials and synthetic fibers. Exemplary materials include polydioxanon (sold under the trademark PDS®), Polyglycerol sebacate (PGS), PGA (Polyglycolic acid and various forms thereof, marketed under the trademarks VICRYL® and/or NEOVEIL®), PCL (Polycaprolactone), PLA or PLLA (Polylactic acid), PHA (Polyhydroxyalkanoate), PGCL (Poliglecaprone 25, sold under the trademark MONOCRYL®, PANACRYL® (Ethicon, Inc., Somerville, N.J.), polyglactin 910, polyglyconate, PGA/TMC (polyglocolide-trimethylene carbonate sold under the trademark BIOSYN®), polyhydroxybutyrate (PHB), poly(vinylpyrrolidone) (PVP), poly(vinyl alcohol) (PVA), absorbable polyurethanes, regenerated cellulose, and oxidized regenerated cellulose fibers (ORC). Blends and/or copolymerizations of any of the aforementioned materials can be tailored to have a desired molecular weight, mechanical properties, and/or degredation rate.

One of skill in the art will understand that the fiber size of the non-woven adjunct can be optimized in order to achieve desired properties. In a preferred embodiment, the fibers can be suture fibers from about 10-0 to 2-0 in size, i.e., about 0.02 mm to 0.3 mm. In a more preferred embodiment, the fibers can be size 7-0, i.e., about 0.15 mm.

Adjuncts Having Mesh and Fibrous Layers

Figure 23:
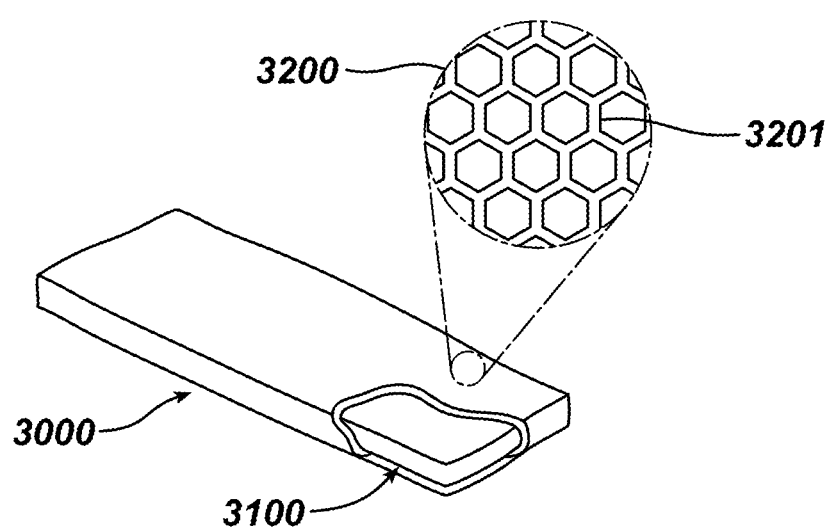
FIG. 23 is a perspective view of an adjunct material that includes a fleece core layer surrounded by woven support layers.

In other embodiments, the adjunct material can have other constructions, such as a woven or non-woven adjunct material surrounded by a mesh. For example, FIG. 23 shows a mesh 3200 formed from fibers 3201, can surround adjunct material 3100. The mesh 3200 can have various configurations, and can include a plurality of fibers 3201 arranged in a repeating pattern such as a honeycomb structure, as shown. The size of mesh, and type of mesh can be varied, in addition to the construction of the non-woven material described above, to modify the mechanical properties of the non-woven material as described above. A mesh can be positioned around a core layer similar to the core layers previously described. For example, the mesh can surround a fleece core layer, or one made from melt blown fibers. The mesh may be used to constrain adjunct material 3100 in a desired state for use. Further, the mesh may be used to facilitate attachment to a stapling device.

In general, the mesh can be a loosely woven mesh of fibers. The mesh can be a mesh of fibers woven in a geometry that is transparent to light. The mesh can have a wide range of pore sizes, such as in the range of about 0.5 to 5 mm.

In general, the mesh material can be a mesh that is suitable for surgical implantation. The mesh can be biocompatible and may be bioabsorbable. In one exemplary embodiment, the mesh can be PROCEED® or PHYSIOMESH®, both of which are manufactured by Ethicon, Inc. of Somerville, N.J.

In certain aspects, the mesh surrounding the fleece material can be coated with a therapeutic agent such that the mesh can elute or release the therapeutic agent to a patient when the adjunct is positioned in a patient's body. The therapeutic agent may be a drug that promotes a beneficial outcome such as healing, or prevents infection.

Coating an Adjunct with a Therapeutic Substance

Figure 21A:
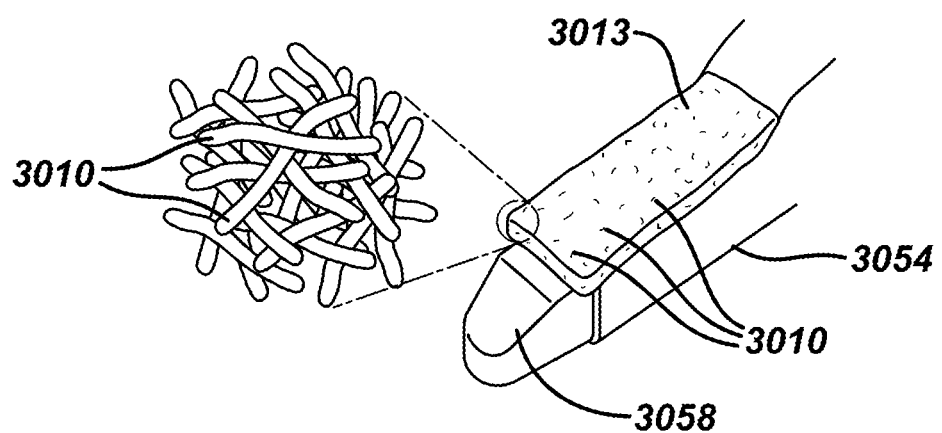
FIG. 21A is a perspective view of an end effector with partial detail of a fibrous adjunct material loaded onto the cartridge assembly.
Figure 21B:
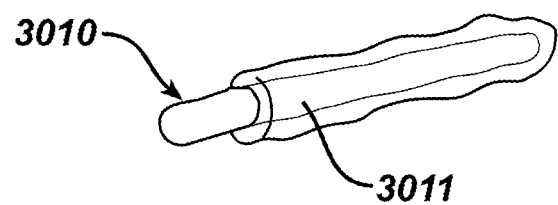
FIG. 21B illustrates a fiber of the adjunct material of FIG. 21A coated with a drug.

The fibers of an adjunct material can be coated with a therapeutic substance i.e., one that can aid in healing and/or combat or prevent infection and that can be effective to be released upon implantation of an adjunct material. For example, FIG. 21A shows an adjunct material 3013, loaded on the tissue facing surface 3058 of an anvil 3054 in which the adjunct material includes fibers 3010 coated with a therapeutic substance 3011 as shown in FIG. 21B. In another embodiment (not shown), the fibers in a woven adjunct material can be coated with a therapeutic substance. One skilled in the art will appreciate that the number/percentage of fibers coated with a therapeutic substance can vary. In another embodiment (not shown), only a small percentage of the fibers of the adjunct material are coated, e.g., in the range of about 5 to 50% of the fibers by volume can be coated.

In some embodiments, the adjunct material may include one or more therapeutic agents, such as, for example, drugs, clotting or sealing agents, antibacterial agent(s), and antimicrobial agent(s). It should be appreciated that any number of any suitable therapeutic substances can be included on an adjunct material. The therapeutic agent can be configured to be released over time to aid the tissue in healing, for example. In embodiments where more than one therapeutic agent is employed, different therapeutic agents can be configured to release at different rates.

Therapeutic substance coated onto the fibers can have various properties. Exemplary therapeutic substances that can be employed can include those that expedite binding as well as antibiotics, and antimicrobials. Exemplary therapeutic substances can include a mixture of fibrinogen and thrombin. In one embodiment, fibrinogen and thrombin can be used as therapeutic substances for coating the VICRYL® suture which forms the adjunct material because lyophilized fibrinogen and thrombin (human or animal derived) are known to adhere to VICRYL® fibers when released from a fluid suspension VICRYL® fibers can be used in the tissue contacting surface. In another embodiment a small number of VICRYL® fibers can be used. In another embodiment, VICRYL® fibers can be woven (e.g., needle punch) into the structure of the adjunct material, e.g. at the core or on the support layers, and can be coated with a therapeutic substance. In certain aspects, when thrombin coated onto a woven adjunct, the thrombin can comprise about 1% or less of the woven adjunct.

As previously mentioned, various antimicrobials can be coated onto the fibers of woven or non-woven adjunct material. Exemplary include, by way of non-limiting example, triclosean and ionized silver. In another embodiment, antibiotics can be deposited only onto a woven layer of an adjunct material. Where a woven layer of an adjunct material includes an antibiotic, antimicrobial, or antibacterial woven therein or coated onto the fibers, the antibiotic/antimicrobial/antibacterial can comprise about 0.5% or less of the adjunct material.

A therapeutic substance can be coated on the fibers of the elastic core layer of a woven adjunct material. When the therapeutic substance is deposited on the fibers of the elastic core, the therapeutic substance can be in liquid form and can be absorbed into the elastic core layer. This can allow the therapeutic substance to disperse into the tissue following implantation of the adjunct material.

An adjunct material can include various other layers. In another embodiment, (not shown), the elastic core layer can have a film coupled to at least one side of the core layer. In an exemplary embodiment the film is made of PDS®. In another embodiment, the film can include PGA/PCL 75/250 polymeric fibers.

Modifying Region(S) of an Adjunct Material Based on Features of a Surgical Device The adjunct material on the cartridge assembly can have varied properties throughout or particular regions of the adjunct material can be modified to correspond to a portion of the end effector to which the adjunct will be coupled. For example, when the adjunct material is to be used on a surgical stapler having a knife, e.g. surgical staplers 10, 100, and 200, the properties of the adjunct can be modified in the region in which the knife will cut through the adjunct material. Such a modification can include thinning out the flexible support layer, using less material, the core layer only at this region, having a more loosely woven layer than other layers of the adjunct, or removing excess material with a laser. In another embodiment, felting can be applied to specified regions of the adjunct so that the knife can more easily penetrate and cut through the adjunct material. In another embodiment, the properties of the adjunct can be modified by either adding or removing fibers from the woven structure to make it stiffer or more flexible, respectively. A zone of increased stiffness may be useful for attachment to the stapling device. In addition, zones of increased flexibility may be help to promote optimal tissue interactions.

A felting process can be used to control dimensions and/or adjust a local density of the adjunct material, such as to decrease a density of a single layer or multiple layers of an adjunct material. Felting can include applying heat to a specific section of the adjunct material at a temperature between the material's glass transition temperature and its melting temperature. By applying heat above the glass transition temperature, and below the melting temperature the structure of the material can be altered. With this process it is possible to decrease the density of the material while avoiding changes associated with complete melting of the material.

Figure 24A:
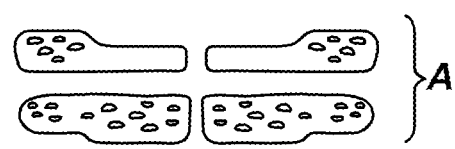
FIG. 24A is a perspective view of four adjunct materials for loading onto an end effector of a stapler.
Figure 24B:
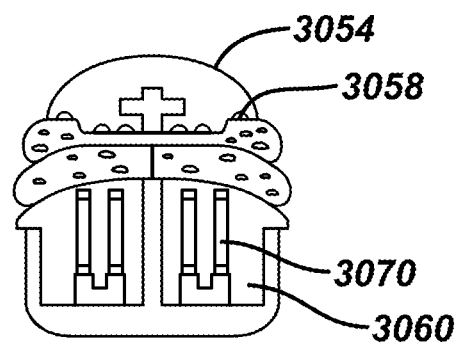
FIG. 24B is an end, sectional view of adjunct materials loaded onto both the anvil and cartridge assembly of a stapler.

In an alternative embodiment, the adjunct material can be used on both the anvil and cartridge side of a surgical stapler. For example, FIGS. 24A and B demonstrate the use of adjunct material A on both the tissue facing surface 3058 of the anvil portion 3054, and the cartridge assembly 3060, wherein the staples 3070 are covered by the adjunct material so that when deployed, the staples can pierce the adjunct material. A thickness of the adjunct material thickness can be varied across a lateral or longitudinal (not shown) length of the anvil and the cartridge assembly, such as by using methods described above. Such an asymmetric geometry on both tissue facing surfaces of the anvil and cartridge may be useful for tissue facing surfaces that are not flat, which may be useful when staples 3070 are of varying unformed height, formed heights, or both unformed and formed heights. In such an arrangement, it is important to note that the geometry of an adjunct material on the first opposing jaw is not necessarily symmetric with the geometry of an adjunct material on the second opposing jaw. In one embodiment the combined thickness of both adjunct materials across a lateral distance is approximately the same. In another embodiment, the combined thickness of both adjunct materials across a lateral distance is not the same.

Stapling Adjunct Material onto Tissue

The adjunct material described herein can be deployed onto tissue using a surgical stapling device, e.g., surgical staplers 10, 100, 200, open linear cutting stapler. In use, tissue can be engaged between a cartridge assembly and an anvil of a surgical stapler at a surgical site, wherein at least one of the cartridge assembly and anvil has an adjunct material releasably retained thereon. The surgical stapler can be actuated to eject staples from the cartridge assembly, through the adjunct material, and into the tissue. The adjunct material can help to reduce impact and trauma from the stapling, evenly distribute strain along the staple line, and can compensate for variable tissue thickness and allow staples secure onto thin or diseased areas of tissue. Different areas of the adjunct material can perform different functions when the adjunct material is stapled onto tissue.

Figure 25A:
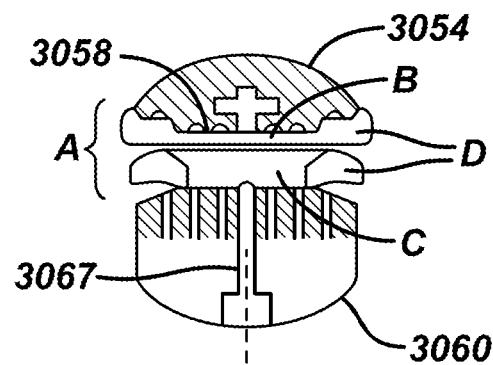
FIG. 25A is a front sectional view of adjunct materials loaded onto both the anvil and cartridge assembly of an end effector.
Figure 25B:
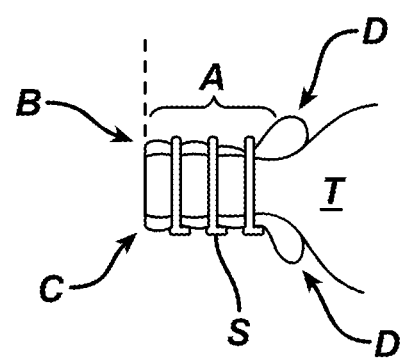
FIG. 25B is a side sectional view of the adjunct material of FIG. 25A stapled onto tissue.

FIG. 25A shows four adjunct materials that can be releasably coupled to an end effector of a surgical stapler. First and second adjunct materials can couple to a tissue facing surface 3058 of the anvil 3054 and second and third adjunct materials can coupled to the cartridge assembly 3060. Three regions of the adjunct material identified as B, C, and D, can each perform a different function. For example, the B region can be used for staple sealing, the D region can be used for stress relief and collateral damage reduction, and the C region can be used for variable thickness compensation. Accordingly, it can be possible to select the adjunct material used in each region to meet desired surgical outcomes. When the adjunct material is deployed onto the tissue T and coupled thereto via the staples S, the adjunct material can be positioned along an outer surface of the tissue, as shown in FIG. 25B. The adjunct material can seal the staples, provide stress relief and reduce collateral damage to nearby tissue, and/or can compensate for variable tissue thickness.

Reprocessing

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

In some embodiments, devices described herein can be processed before surgery. First, a new or used instrument, which can include an adjunct material, is obtained and if necessary cleaned. The instrument can then be sterilized. In some embodiments, the instrument can be dried, e.g., in an oven, together with a desiccant item, which can have a greater affinity for moisture than the adjunct material. In one sterilization technique, the instrument is placed in a closed and sealed container, such as a plastic or TYVEK bag or a foil bag. The container and instrument are then placed in a field of radiation that can penetrate the container, such as gamma radiation, x-rays, or high-energy electrons. The radiation kills bacteria on the instrument and in the container. In another sterilization technique, the instrument is placed in a first container, such as a plastic or TYVEK bag, having a vapor permeable backing. The first container can then be packaged in a second container, e.g., a foil bag, which can be left open. The first and second containers, together with the instrument, can undergo ethylene oxide sterilization. The second container can then be sealed to prevent moisture exposure. Prior to sealing, a desiccant item may be included in at least one of the first and second containers to further prevent changes to one or more device components. In both techniques, the sterilized materials can then be stored in the sterile container(s) to keep the materials sterile until the container(s) is/are opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A staple cartridge for use with a surgical stapler, comprising:
 a cartridge body having a plurality of staple cavities configured to seat staples therein; and
 a biocompatible, compressible adjunct material releasably retained on the cartridge body and configured to be delivered to tissue by deployment of the staples in the cartridge body, the material having a compressible elastic core layer configured to compress upon application of a compressive force and expand upon removal of the compressive force, the compressible elastic core layer having woven fibers oriented such that the woven fibers are looser in a direction of the compression than in a second direction perpendicular to the direction of the compression, and at least one flexible support layer coupled to at least a first surface of the compressible elastic core layer.

2. The staple cartridge of claim 1, wherein the flexible support layer is coupled to the first surface and to an opposed second surface of the compressible elastic core layer.

3. The staple cartridge of claim 1, wherein the flexible support layer is coupled to the surface of the compressible elastic core by an interlocking weave.

4. The staple cartridge of claim 1, wherein the flexible support layer is adhered to the surface of the compressible elastic core layer.

5. The staple cartridge of claim 1, wherein the flexible support layer is comprised of woven fibers interlocked in the X and Y dimensions.

6. The staple cartridge of claim 5, wherein the fibers of the flexible support layer are comprised of a biocompatible, absorbable suture material, selected from the group consisting of polydioxanon, Polyglycerol sebacate, Polyglycolic acid, Polycaprolactone, Polylactic acid, Polyhydroxyalkanoate, Poliglecaprone 25, polyglactin 910, polyglyconate, polyglocolide-trimethylene carbonate, polyhydroxybutyrate, poly(vinylpyrrolidone), poly(vinyl alcohol), absorbable polyurethanes, regenerated cellulose, and oxidized regenerated cellulose fibers.

7. The staple cartridge of claim 5, wherein the fibers of the flexible support layer are comprised of suture filaments having a size in the range of about 8-0 to 4-0.

8. The staple cartridge of claim 5, wherein the woven fibers of the flexible support layer are woven around and interlocked with the woven fibers of the compressible elastic core layer.

9. The staple cartridge of claim 1, wherein the flexible support layer comprises a film.

10. The staple cartridge of claim 1, wherein the woven fibers of the elastic core are non-interlocked woven fibers.

11. The staple cartridge of claim 1, wherein a weave density of the elastic core layer is less dense than a weave density of the flexible support layers.

12. The staple cartridge of claim 1, wherein the woven fibers of the elastic core layer have a size in the range of about 0 to 0-0.

13. The staple cartridge of claim 1, wherein the adjunct material is selectively stiffened in certain regions.

14. The staple cartridge of claim 1, wherein the adjunct material is comprised of a fleece, the fleece having a first density in the compressible elastic core layer and a second, different density in the flexible support layer.

15. The staple cartridge of claim 1, wherein the woven fibers of the compressible elastic core layer oriented in the second direction are compacted to resist compression.

16. An end effector for a surgical instrument, comprising:
 a first jaw having a cartridge body removably attached hereto, the cartridge body having a plurality of staple cavities configured to seat staples therein;
 a second jaw having an anvil with a plurality of staples forming openings formed therein, wherein at least one of the first and second jaws is movable relative to the other; and
 a tissue reinforcement comprising (i) a compressible elastic region configured to compress upon application of a compressive force and expand upon removal of the compressive force and (ii) a flexible support layer coupled to at least one surface of the compressible elastic core, wherein at least one of the compressible elastic region and the flexible support layer has a central region that is more dense than regions adjacent a perimeter of the at least one of the compressible elastic region or the flexible support layer, and wherein the tissue reinforcement is releasably retained on at least one of the tissue contacting surfaces of the cartridge body and the anvil for delivery to a tissue upon deployment of staples from the cartridge body through the compressible elastic region.

17. The end effector of claim 16, wherein the central region is not transparent to light.

18. A method for implanting a tissue reinforcement, comprising;

engaging tissue between a cartridge assembly and an anvil of a surgical stapler at a surgical site, at least one of the cartridge assembly and anvil having a tissue reinforcement releasably retained thereon wherein, the tissue reinforcement comprises a compressible elastic core configured to compress upon application of a compressive force and expand upon removal of the compressive force and a flexible support layer surrounding all sides of the compressible elastic core so as to envelop the elastic core; and actuating the surgical stapler to eject staples from the cartridge assembly through the compressible elastic region and into the tissue, to maintain the tissue reinforcement at the surgical site.

19. The method of claim 18, wherein the compressible elastic core layer is formed of a woven material that is more loosely woven than a woven material forming the flexible support layer.

* * * * *